(12) United States Patent
Igarashi et al.

(10) Patent No.: US 8,609,259 B2
(45) Date of Patent: Dec. 17, 2013

(54) ORGANIC ELECTROLUMINESCENT DEVICE AND PLATINUM COMPOUND

(75) Inventors: Tatsuya Igarashi, Minami-ashigara (JP); Kousuke Watanabe, Minami-ashigara (JP); Seiji Ichijima, Minami-ashigara (JP); Toshihiro Ise, Minami-ashigara (JP)

(73) Assignee: UDC Ireland Limited, Dublin (IE)

( * ) Notice: Subject to any disclaimer, the term of this patent is extended or adjusted under 35 U.S.C. 154(b) by 0 days.

(21) Appl. No.: 13/586,748

(22) Filed: Aug. 15, 2012

(65) Prior Publication Data

US 2012/0306360 A1    Dec. 6, 2012

Related U.S. Application Data

(62) Division of application No. 12/571,093, filed on Sep. 30, 2009, now Pat. No. 8,257,838, which is a division of application No. 10/548,669, filed as application No. PCT/JP2004/006498 on May 7, 2004, now Pat. No. 7,615,633.

(30) Foreign Application Priority Data

May 9, 2003  (JP) ................. 2003-132257
Mar. 25, 2004 (JP) ................. 2004-88575

(51) Int. Cl.
*H01L 51/54*   (2006.01)
*C09K 11/06*   (2006.01)

(52) U.S. Cl.
USPC ..... 428/690; 428/917; 313/504; 257/E51.044

(58) Field of Classification Search
None
See application file for complete search history.

(56) References Cited

U.S. PATENT DOCUMENTS

| | | | |
|---|---|---|---|
| 6,303,231 B1 | 10/2001 | Sawada et al. | |
| 6,303,238 B1 | 10/2001 | Thompson et al. | |
| 6,653,564 B2 | 11/2003 | Scheidle | |
| 6,653,654 B1 | 11/2003 | Che | |
| 7,566,505 B2 | 7/2009 | Ise et al. | |
| 7,569,692 B2 | 8/2009 | Nii et al. | |
| 7,579,093 B2 | 8/2009 | Sano et al. | |
| 7,655,323 B2 * | 2/2010 | Walters et al. ............ | 428/690 |
| 7,771,845 B2 | 8/2010 | Sano et al. | |
| 7,947,383 B2 | 5/2011 | Ise et al. | |
| 7,960,040 B2 | 6/2011 | Okada | |
| 2002/0008233 A1 | 1/2002 | Forrest et al. | |
| 2002/0013306 A1 | 1/2002 | Lowe | |
| 2002/0068190 A1 | 6/2002 | Tsuboyama et al. | |
| 2002/0115566 A1 | 8/2002 | Sessler et al. | |
| 2003/0152802 A1 | 8/2003 | Tsuboyama et al. | |
| 2003/0205707 A1 | 11/2003 | Chi-Ming | |
| 2005/0170206 A1 | 8/2005 | Ma et al. | |
| 2005/0170209 A1 | 8/2005 | Lee et al. | |
| 2006/0073359 A1 | 4/2006 | Ise et al. | |
| 2006/0134460 A1 | 6/2006 | Kondakova et al. | |
| 2006/0134461 A1 | 6/2006 | Huo et al. | |

(Continued)

FOREIGN PATENT DOCUMENTS

EP    0 278 757 A2    8/1988
EP    0 969 532 A2    1/2000

(Continued)

OTHER PUBLICATIONS

Mario Bossa et al.; "On the electronic states of the extended porphyrin family"; Journal of Molecular Structure (Theochem) vol. 342, 1995, pp. 73-86.

(Continued)

*Primary Examiner* — Marie R. Yamnitzky
(74) *Attorney, Agent, or Firm* — Morgan, Lewis & Bockius LLP

(57) ABSTRACT

An organic electroluminescent device, which has a pair of electrodes, and at least one organic layer including a luminescent layer between the electrodes, wherein the organic layer contains at least one compound of formula (1):

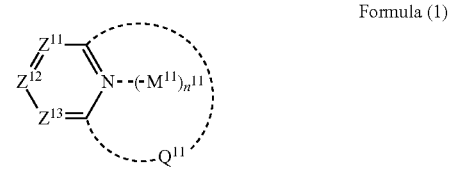

Formula (1)

wherein $Q^{11}$ are atoms for forming a nitrogen-containing hetero ring; $Z^{11}$ to $Z^{13}$ each independently represents CR, wherein R represents a substituent, CH or N; $n^{11}$ is 0 or 1; $M^{11}$ is a metal or boron ion that may further have a ligand(s); and a compound of formula (6):

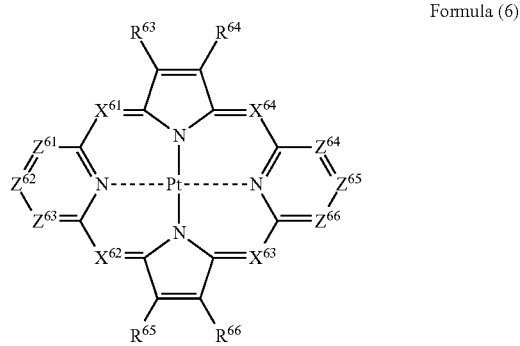

Formula (6)

wherein $R^{63}$ to $R^{66}$ each is a hydrogen atom or a substituent; $X^{61}$ to $X^{64}$ and $Z^{61}$ to $Z^{66}$ each is CR, wherein R represents a substituent, CH or N.

3 Claims, No Drawings

(56) References Cited

U.S. PATENT DOCUMENTS

| | | |
|---|---|---|
| 2006/0182992 A1 | 8/2006 | Nii et al. |
| 2006/0264625 A1 | 11/2006 | Nakayama et al. |
| 2006/0286406 A1 | 12/2006 | Igarashi et al. |
| 2007/0082284 A1 | 4/2007 | Stoessel et al. |
| 2007/0103060 A1 | 5/2007 | Itoh et al. |
| 2008/0001530 A1 | 1/2008 | Ise et al. |
| 2008/0036373 A1 | 2/2008 | Itoh et al. |
| 2009/0128008 A1 | 5/2009 | Ise et al. |

FOREIGN PATENT DOCUMENTS

| | | | |
|---|---|---|---|
| JP | 5751781 | A | 3/1982 |
| JP | 595566 | A | 1/1984 |
| JP | 5-9470 | A | 1/1993 |
| JP | 09-013024 | A3 | 1/1997 |
| JP | 2000-048960 | A | 2/2000 |
| JP | 2000-503982 | A | 4/2000 |
| JP | 2001-338768 | A | 12/2001 |
| JP | 2002-175884 | A | 6/2002 |
| JP | 2002-280180 | A | 9/2002 |
| JP | 2002-305083 | A | 10/2002 |
| JP | 2002-363552 | A | 12/2002 |
| JP | 2003-73355 | A | 3/2003 |
| JP | 2003-123976 | A | 4/2003 |
| JP | 2003-123981 | A | 4/2003 |
| JP | 2003-123983 | A | 4/2003 |
| JP | 2003-142271 | A | 5/2003 |
| JP | 2003-520391 | A | 7/2003 |
| JP | 2004-331508 | A | 11/2004 |
| JP | 2005-220136 | A | 8/2005 |
| JP | 2005-310733 | A | 11/2005 |
| JP | 2006-093542 | A | 4/2006 |
| JP | 2006-120811 | A | 5/2006 |
| JP | 2006-256999 | A | 9/2006 |
| JP | 2006-261623 | A | 9/2006 |
| JP | 2006-332620 | A | 12/2006 |
| JP | 2007-019462 | A | 1/2007 |
| JP | 2007-073845 | A | 3/2007 |
| JP | 2007-519614 | A | 7/2007 |
| JP | 2008-037848 | A | 2/2008 |
| JP | 2008-103535 | A | 5/2008 |
| JP | 2008-524848 | A | 7/2008 |
| WO | 99/20081 | A2 | 4/1999 |
| WO | 00/57676 | A1 | 9/2000 |
| WO | 0070655 | A2 | 11/2000 |
| WO | 03/093283 | A1 | 11/2003 |
| WO | 2004/039914 | A1 | 5/2004 |
| WO | 2004/099339 | A1 | 11/2004 |
| WO | 2004/108857 | A1 | 12/2004 |
| WO | 2005/042444 | A2 | 5/2005 |
| WO | 2005/042550 | A1 | 5/2005 |
| WO | 2005/112520 | A1 | 11/2005 |

OTHER PUBLICATIONS

Shigeya Kobayashi et al.; "Shape-persistent cyclyne-type azamacrocycles: synthesis, unusual light-emitting characteristics, and specific recognition of the Sb(V) ion"; Tetrahedron Letters; vol. 44, 2003, pp. 1469-1472.

Japanese Office Action and Translation issued in corresponding Japanese Application No. 2004-279153 (dated Nov. 11, 2009) of U.S. Appl. No. 12/395,542.

Baldo et al, Nature 395, pp. 151-154, (1998).

Che et al., Chem. Eur. J. 9(6), pp. 1263-1272, (2003).

Japanese Office Action (with English translation) dated Jun. 29, 2010 issued in corresponding Japanese Application No. 2010-002388 of U.S. Appl. No. 12/395,542.

U.S. Office Action issued on Aug. 30, 2011 in the co-pending U.S. Appl. No. 12/395,542.

Machine-assisted translation of JP 2003-123983 (Apr. 2003).

Machine-assisted translation of JP 2003-142271 (May 2003).

\* cited by examiner

ORGANIC ELECTROLUMINESCENT DEVICE AND PLATINUM COMPOUND

CROSS-REFERENCE TO RELATED APPLICATIONS

This application is a Divisional of U.S. application Ser. No. 12/571,093 filed Sep. 30, 2009, now U.S. Pat. No. 8,257,838 which is a Divisional of U.S. application Ser. No. 10/548,669 filed Sep. 9, 2005, now U.S. Pat. No. 7,615,633, which is a 371 of PCT/JP2004/006498 filed May 7, 2004, which claims benefit of JPA No. 2003-132257 filed May 9, 2003 and JPA No. 2004-88575 filed Mar. 25, 2004. The above-noted applications are incorporated herein by reference in their entirety.

TECHNICAL FIELD

The present invention relates to a luminescent device, particularly an organic electroluminescent device (hereinafter sometimes referred to as an EL device), and to a platinum compound that is useful in the luminescent device.

BACKGROUND ART

Recently, a variety of types of display devices are actively researched and developed. Among these, much attention is focused on organic electroluminescent (EL) devices. This is because organic EL devices are promising display devices capable of emitting light of high luminance under low applied voltage. An important characteristic of organic EL devices is life (durability), and as such, studies have been made toward further prolonging the life of organic EL devices. As a means to prolong life, luminescent devices of a type comprising a hole-injection layer containing CuPc (copper phthalocyanine) are known (as described, for example, in JP-A-57-51781 ("JP-A" means unexamined published Japanese patent application) and Applied Physics Letters, 15, 69, 1996). However, such luminescent devices are still low in quantum efficiency. Accordingly, there is a demand for further improved devices.

On the other hand, for the development of organic EL devices in recent years, various studies have aimed at improving the external quantum efficiency of the devices. In particular, observation is focused on luminescent devices containing a phosphorescent material, such as tris-phenylpyridine iridium complexes (see WO 00/070655) and tetradentate platinum complexes (for example, octaethylporphyrin platinum complexes) (see U.S. Pat. No. 6,303,238 B1 and No. 6,653,564 B1), because high-external quantum efficiency is attained with these devices. However, these phosphorescent materials and devices containing the phosphorescent material have needed life prolongation. In addition, conventional tetradentate platinum complexes (see U.S. Pat. No. 6,303,238 B1 and No. 6,653,564 B1) have the problem that light emission is restricted to the color ranging from orange to red, and therefore it is difficult to obtain light emission in the short wavelength ranging from blue to green that is necessary for use in full color displays and multicolor displays.

DISCLOSURE OF THE INVENTION

According to the present invention, there are provided the following means:

(1) An organic electroluminescent device, comprising a pair of electrodes, and at least one organic layer including a luminescent layer between the electrodes, wherein said organic layer comprises at least one compound represented by formula (1):

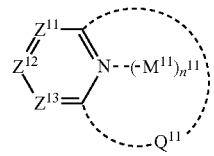

Formula (1)

wherein, in formula (1), $Q^{11}$ represents a group of atoms for forming a nitrogen-containing hetero ring; $Z^{11}$, $Z^{12}$ and $Z^{13}$ each represent a substituted or unsubstituted carbon atom or nitrogen atom; $n^{11}$ represents 0 or 1; $M^{11}$ represents a metal ion or a boron ion, each of which may further have a ligand(s).

(2) The organic electroluminescent device as described in the item (1), wherein the compound represented by formula (1) is a compound represented by formula (11):

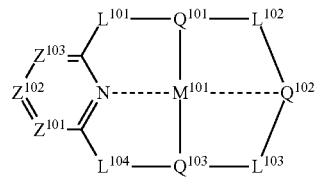

Formula (11)

wherein, in formula (11), $Z^{101}$, $Z^{102}$ and $Z^{103}$ each represent a substituted or unsubstituted carbon atom or nitrogen atom; $L^{101}$, $L^{102}$, $L^{103}$ and $L^{104}$ each represent a single bond or a linking group; $Q^{101}$ and $Q^{103}$ each represent a group containing a carbon, nitrogen, phosphorus, oxygen or sulfur atom as a coordinating atom to $M^{101}$ respectively; $Q^{102}$ represents a group containing a nitrogen, phosphorus, oxygen or sulfur atom as a coordinating atom to $M^{101}$; and $M^{101}$ represents a metal ion that may further have a ligand(s).

(3) The organic electroluminescent device as described in the item (1), wherein the compound represented by formula (1) is a compound represented by formula (15):

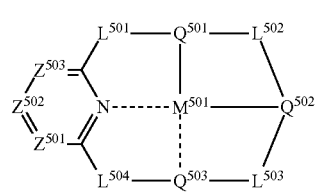

Formula (15)

wherein, in formula (15), $Z^{501}$, $Z^{502}$ and $Z^{503}$ each represent a substituted or unsubstituted carbon atom or nitrogen atom; $L^{501}$, $L^{502}$, $L^{503}$ and $L^{504}$ each represent a single bond or a linking group; $Q^{501}$ and $Q^{502}$ each represent a group containing a carbon, nitrogen, phosphorus, oxygen or sulfur atom as a coordinating atom to $M^{501}$ respectively; $Q^{503}$ represents a group containing a nitrogen, phosphorus, oxygen or sulfur atom as a coordinating atom to $M^{501}$; and $M^{501}$ represents a metal ion that may further have a ligand(s).

(4) The organic electroluminescent device as described in the item (2), wherein the compound represented by formula (11) is a compound represented by formula (2) or (3):

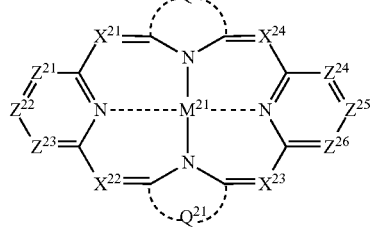

Formula (2)

wherein, in formula (2), $Q^{21}$ and $Q^{22}$ each represent a group for forming a nitrogen-containing hetero ring; $X^{21}$, $X^{22}$, $X^{23}$ and $X^{24}$ each represent a substituted or unsubstituted carbon atom or nitrogen atom; $Z^{21}$, $Z^{22}$, $Z^{23}$, $Z^{24}$, $Z^{25}$, and $Z^{26}$ each represent a substituted or unsubstituted carbon atom or nitrogen atom; $M^{21}$ represents a metal ion that may further have a ligand(s);

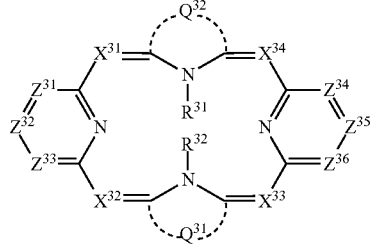

Formula (3)

wherein, in formula (3), $R^{31}$ and $R^{32}$ each represent a hydrogen atom or a substituent; $Q^{31}$ and $Q^{32}$ each represent a group for forming a nitrogen-containing hetero ring; $X^{31}$, $X^{32}$, $X^{33}$ and $X^{34}$ each represent a substituted or unsubstituted carbon atom or nitrogen atom; $Z^{31}$, $Z^{32}$, $Z^{33}$, $Z^{34}$, $Z^{35}$, and $Z^{36}$ each represent a substituted or unsubstituted carbon atom or nitrogen atom.

(5) The organic electroluminescent device as described in the item (4), wherein the compound represented by formula (2) is a compound represented by formula (4):

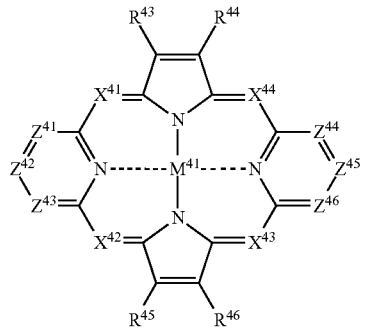

Formula (4)

wherein, in formula (4), $R^{43}$, $R^{44}$, $R^{45}$ and $R^{46}$ each represent a hydrogen atom or a substituent; $X^{41}$, $X^{42}$, $X^{43}$ and $X^{44}$ each represent a substituted or unsubstituted carbon atom or nitrogen atom; $Z^{41}$, $Z^{42}$, $Z^{43}$, $Z^{44}$, $Z^{45}$ and $Z^{46}$ each represent a substituted or unsubstituted carbon atom or nitrogen atom; $M^{41}$ represents a metal ion that may further have a ligand(s).

(6) The organic electroluminescent device as described in the item (4), wherein the compound represented by formula (3) is a compound represented by formula (5):

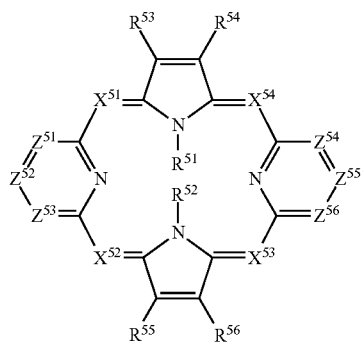

Formula (5)

wherein, in formula (5), $R^{51}$, $R^{52}$, $R^{53}$, $R^{54}$, $R^{55}$ and $R^{56}$ each represent a hydrogen atom or a substituent; $X^{51}$, $X^{52}$, $X^{53}$ and $X^{54}$ each represent a substituted or unsubstituted carbon atom or nitrogen atom; $Z^{51}$, $Z^{52}$, $Z^{53}$, $Z^{54}$, $Z^{55}$ and $Z^{56}$ each represent a substituted or unsubstituted carbon atom or nitrogen atom.

(7) The organic electroluminescent device as described in the item (2), wherein the compound represented by formula (11) is a compound represented by formula (12) or a tautomer thereof:

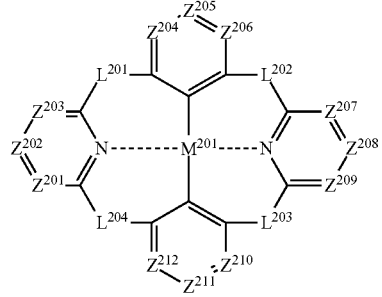

Formula (12)

wherein, in formula (12), $Z^{201}$, $Z^{202}$, $Z^{203}$, $Z^{204}$, $Z^{205}$, $Z^{206}$, $Z^{207}$, $Z^{208}$, $Z^{209}$, $Z^{210}$, $Z^{211}$, and $Z^{212}$ each represent a substituted or unsubstituted carbon atom or nitrogen atom; $L^{201}$, $L^{202}$, $L^{203}$ and $L^{204}$ each represent a single bond or a linking group; and $M^{201}$ represents a metal ion that may further have a ligand(s).

(8) The organic electroluminescent device as described in the item (2), wherein the compound represented by formula (11) is a compound represented by formula (13) or a tautomer thereof:

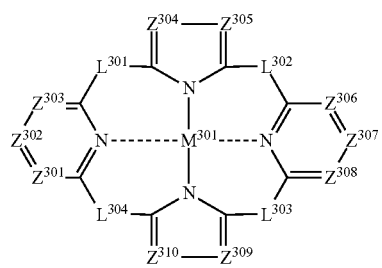

Formula (13)

wherein, in formula (13), $Z^{301}, Z^{302}, Z^{303}, Z^{304}, Z^{305}, Z^{306}, Z^{307}, Z^{308}, Z^{309}$, and $Z^{310}$ each represent a substituted or unsubstituted carbon atom or nitrogen atom; $L^{301}, L^{302}, L^{303}$ and $L^{304}$ each represent a single bond or a linking group; and $M^{301}$ represents a metal ion that may further have a ligand(s).

(9) The organic electroluminescent device as described in the item (2), wherein the compound represented by formula (11) is a compound represented by formula (14) or a tautomer thereof:

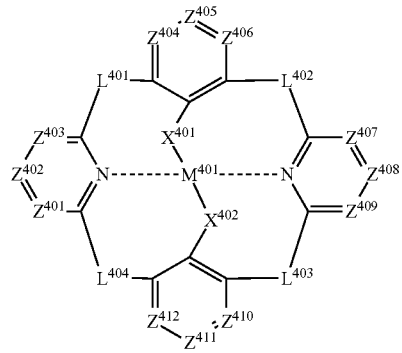

Formula (14)

wherein, in formula (14), $Z^{401}, Z^{402}, Z^{403}, Z^{404}, Z^{405}, Z^{406}, Z^{407}, Z^{408}, Z^{409}, Z^{410}, Z^{411}$, and $Z^{412}$ each represent a substituted or unsubstituted carbon atom or nitrogen atom; $L^{401}, L^{402}, L^{403}$ and $L^{404}$ each represent a single bond or a linking group; $M^{401}$ represents a metal ion that may further have a ligand(s); and $X^{401}$ and $X^{402}$ each represent an oxygen atom, a substituted or unsubstituted nitrogen atom, or a sulfur atom.

(10) The organic electroluminescent device as described in the item (3), wherein the compound represented by formula (15) is a compound represented by formula (16) or a tautomer thereof:

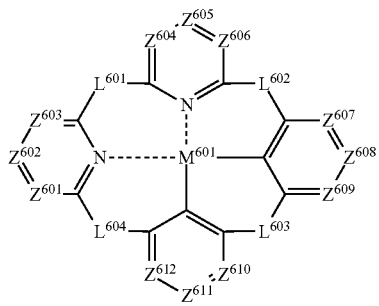

Formula (16)

wherein, in formula (16), $Z^{601}, Z^{602}, Z^{603}, Z^{604}, Z^{605}, Z^{606}, Z^{607}, Z^{608}, Z^{609}, Z^{610}, Z^{611}$, and $Z^{612}$ each represent a substituted or unsubstituted carbon atom or nitrogen atom; $L^{601}, L^{602}, L^{603}$ and $L^{604}$ each represent a single bond or a linking group; and $M^{601}$ represents a metal ion that may further have a ligand(s).

(11) The organic electroluminescent device as described in the item (3), wherein the compound represented by formula (15) is a compound represented by formula (17) or a tautomer thereof:

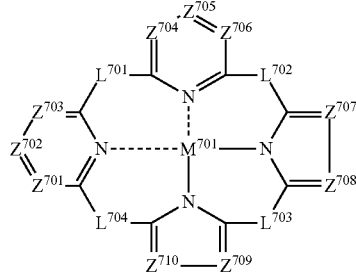

Formula (17)

wherein, in formula (17), $Z^{701}, Z^{702}, Z^{703}, Z^{704}, Z^{705}, Z^{706}, Z^{707}, Z^{708}, Z^{709}$, and $Z^{710}$ each represent a substituted or unsubstituted carbon atom or nitrogen atom; $L^{701}, L^{702}, L^{703}$ and $L^{704}$ each represent a single bond or a linking group; and $M^{701}$ represents a metal ion that may further have a ligand(s).

(12) The organic electroluminescent device as described in the item (3), wherein the compound represented by formula (15) is a compound represented by formula (18) or a tautomer thereof:

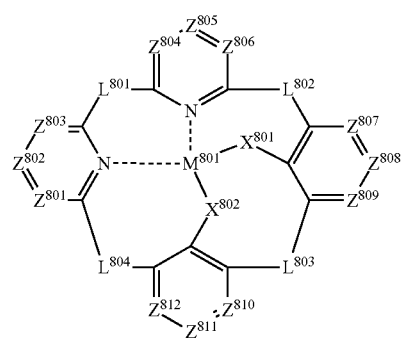

Formula (18)

wherein, in formula (18), $Z^{801}, Z^{802}, Z^{803}, Z^{804}, Z^{805}, Z^{806}, Z^{807}, Z^{808}, Z^{809}, Z^{810}, Z^{811}$, and $Z^{812}$ each represent a substituted or unsubstituted carbon atom or nitrogen atom; $L^{801}, L^{802}, L^{803}$ and $L^{804}$ each represent a single bond or a linking group; $M^{801}$ represents a metal ion that may further have a ligand(s); and $X^{801}$ and $X^{802}$ each represent an oxygen atom, a substituted or unsubstituted nitrogen atom, or a sulfur atom.

(13) The organic electroluminescent device as described in any one of the items (1) to (12), wherein the organic layer is at least one of a luminescent layer and a positive hole-injection layer.

(14) A compound represented by formula (6):

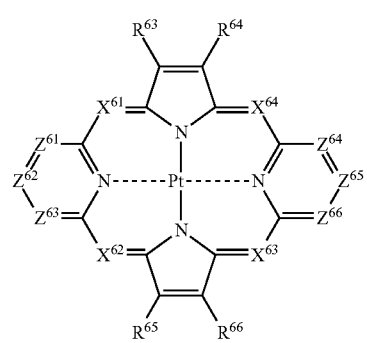

Formula (6)

wherein, in formula (6), $R^{63}$, $R^{64}$, $R^{65}$ and $R^{66}$ each represent a hydrogen atom or a substituent; $X^{61}$, $X^{62}$, $X^{63}$ and $X^{64}$ each represent a substituted or unsubstituted carbon atom or nitrogen atom; $Z^{61}$, $Z^{62}$, $Z^{63}$, $Z^{64}$, $Z^{65}$ and $Z^{66}$ each represent a substituted or unsubstituted carbon atom or nitrogen atom.

(15) The organic electroluminescent device as described in any one of the items (1) to (13), wherein the compound represented by any of formulae (1) to (17) emits a phosphorescence.

(16) The organic electroluminescent device as described in any one of the items (1) to (13) and (15), wherein the luminescent (light-emitting) layer contains at least one host material, and at least one of the compounds represented by any of formulae (1) to (13).

(17) The organic electroluminescent device as described in the item (16), wherein the host material in the light-emitting layer is a complex.

(18) The organic electroluminescent device as described in the item (16) or (17), wherein the light-emitting layer contains at least two host materials.

Other and further features and advantages of the invention will appear more fully from the following description.

BEST MODE FOR CARRYING OUT THE INVENTION

The present invention will be described in detail below.

First, the compound represented by formula (1) will be described.

$Q^{11}$ represents a group of atoms that form a nitrogen-containing hetero ring, together with two carbon atoms bonding to the $Q^{11}$ and a nitrogen atom directly bonding to the carbon atoms. The number of ring member of the nitrogen-containing hetero ring formed by $Q^{11}$ is not particularly limited, but preferably in the range of 12 to 20, more preferably in the range of 14 to 16, and further more preferably 16.

$Z^{11}$, $Z^{12}$ and $Z^{13}$ each represent a substituted or unsubstituted carbon atom or nitrogen atom. As a combination of $Z^{11}$, $Z^{12}$ and $Z^{13}$, it is preferable that at least one of $Z^{11}$, $Z^{12}$ and $Z^{13}$ is a nitrogen atom. Examples of the substituent on the carbon atom include an alkyl group (preferably having 1 to 30 carbon atoms, more preferably having 1 to 20 carbon atoms, and particularly preferably having 1 to 10 carbon atoms, e.g., methyl, ethyl, iso-propyl, tert-butyl, n-octyl, n-decyl, n-hexadecyl, cyclopropyl, cyclopentyl, cyclohexyl), an alkenyl group (preferably having 2 to 30 carbon atoms, more preferably having 2 to 20 carbon atoms, and particularly preferably having 2 to 10 carbon atoms, e.g., vinyl, allyl, 2-butenyl, 3-pentenyl), an alkynyl group (preferably having 2 to 30 carbon atoms, more preferably having 2 to 20 carbon atoms, and particularly preferably having 2 to 10 carbon atoms, e.g., propargyl, 3-pentynyl), an aryl group (preferably having 6 to 30 carbon atoms, more preferably having 6 to 20 carbon atoms, and particularly preferably having 6 to 12 carbon atoms, e.g., phenyl, p-methylphenyl, naphthyl, anthranyl), an amino group (preferably having 0 to 30 carbon atoms, more preferably having 0 to 20 carbon atoms, and particularly preferably having 0 to 10 carbon atoms, e.g., amino, methylamino, dimethylamino, diethylamino, dibenzylamino, diphenylamino, ditolylamino), an alkoxy group (preferably having 1 to 30 carbon atoms, more preferably having 1 to 20 carbon atoms, and particularly preferably having 1 to 10 carbon atoms, e.g., methoxy, ethoxy, butoxy, 2-ethylhexyloxy), an aryloxy group (preferably having 6 to 30 carbon atoms, more preferably having 6 to 20 carbon atoms, and particularly preferably having 6 to 12 carbon atoms, e.g., phenyloxy, 1-naphthyloxy, 2-naphthyloxy), a hetero ring oxy group (preferably having 1 to 30 carbon atoms, more preferably having 1 to 20 carbon atoms, and particularly preferably having 1 to 12 carbon atoms, e.g., pyridyloxy, pyrazyloxy, pyrimidyloxy, quinolyloxy), an acyl group (preferably having 1 to 30 carbon atoms, more preferably having 1 to 20 carbon atoms, and particularly preferably having 1 to 12 carbon atoms, e.g., acetyl, benzoyl, formyl, pivaloyl), an alkoxycarbonyl group (preferably having 2 to 30 carbon atoms, more preferably having 2 to 20 carbon atoms, and particularly preferably having 2 to 12 carbon atoms, e.g., methoxycarbonyl, ethoxycarbonyl), an aryloxycarbonyl group (preferably having 7 to 30 carbon atoms, more preferably having 7 to 20 carbon atoms, and particularly preferably having 7 to 12 carbon atoms, e.g., phenyloxycarbonyl), an acyloxy group (preferably having 2 to 30 carbon atoms, more preferably having 2 to 20 carbon atoms, and particularly preferably having 2 to 10 carbon atoms, e.g., acetoxy, benzoyloxy), an acylamino group (preferably having 2 to 30 carbon atoms, more preferably having 2 to 20 carbon atoms, and particularly preferably having 2 to 10 carbon atoms, e.g., acetylamino, benzoylamino), an alkoxycarbonylamino group (preferably having 2 to 30 carbon atoms, more preferably having 2 to 20 carbon atoms, and particularly preferably having 2 to 12 carbon atoms, e.g., methoxycarbonylamino), an aryloxycarbonylamino group (preferably having 7 to 30 carbon atoms, more preferably having 7 to 20 carbon atoms, and particularly preferably having 7 to 12 carbon atoms, e.g., phenyloxycarbonylamino), a sulfonylamino group (preferably having 1 to 30 carbon atoms, more preferably having 1 to 20 carbon atoms, and particularly preferably having 1 to 12 carbon atoms, e.g., methanesulfonylamino, benzenesulfonylamino), a sulfamoyl group (preferably having 0 to 30 carbon atoms, more preferably having 0 to 20 carbon atoms, and particularly preferably having 0 to 12 carbon atoms, e.g., sulfamoyl, methylsulfamoyl, dimethylsulfamoyl, phenylsulfamoyl), a carbamoyl group (preferably having 1 to 30 carbon atoms, more preferably having 1 to 20 carbon atoms, and particularly preferably having 1 to 12 carbon atoms, e.g., carbamoyl, methylcarbamoyl, diethylcarbamoyl, phenylcarbamoyl), an alkyl thio group (preferably having 1 to 30 carbon atoms, more preferably having 1 to 20 carbon atoms, and particularly preferably having 1 to 12 carbon atoms, e.g., methylthio, ethylthio), an aryl thio group (preferably having 6 to 30 carbon atoms, more preferably having 6 to 20 carbon atoms, and particularly preferably having 6 to 12 carbon atoms, e.g., phenylthio), a hetero ring thio group (preferably having 1 to 30 carbon atoms, more preferably having 1 to 20 carbon atoms, and particularly preferably having 1 to 12 carbon atoms, e.g., pyridyl thio, 2-benzimidazolyl thio, 2-benzoxazoly thio, 2-benzthiazolyl thio), a sulfonyl group (preferably having 1 to 30 carbon atoms, more preferably having 1 to 20 carbon atoms, and particularly preferably having 1 to 12 carbon atoms, e.g., mesyl, tosyl), a sulfinyl group (preferably having 1 to 30 carbon atoms, more preferably having 1 to 20 carbon atoms, and particularly preferably having 1 to 12 carbon atoms, e.g., methanesulfinyl, benzenesulfinyl), a ureido group (preferably having 1 to 30 carbon atoms, more preferably having 1 to 20 carbon atoms, and particularly preferably having 1 to 12 carbon atoms, e.g., ureido, methylureido, phenylureido), a phosphoric acid amido group (preferably having 1 to 30 carbon atoms, more preferably having 1 to 20 carbon atoms, and particularly preferably having 1 to 12 carbon atoms, e.g., diethyl phosphoamido, phenyl phosphoamido), a hydroxyl group, a mercapto group, a halogen atom (e.g., fluorine, chlorine, bromine, iodine), a cyano group, a sulfo group, a carboxyl group, a nitro group, a hydroxamic acid group, a sulfino group, a hydrazino group, an imino group, a heterocyclic group (preferably having 1 to 30 carbon atoms, more preferably having 1 to carbon atoms, and containing a hetero atom such as nitrogen, oxygen and sulfur, preferably being a hetero aryl group, specifically for example, imidazolyl, pyridyl, quinolyl, furyl, thienyl, piperidyl, morpholino, benzoxazolyl, benzimidazolyl, benzthiazolyl, carbazolyl, azepinyl), a silyl group (preferably having 3 to 40 carbon atoms, more preferably having 3 to 30 carbon atoms, and particularly preferably having 3 to 24 carbon atoms, e.g., trimethylsilyl, triphenylsilyl), and a silyloxy group (preferably having 3 to 40 carbon atoms; more preferably having 3 to 30 carbon atoms, and particularly preferably having 3 to 24 carbon atoms, e.g., trimethylsilyloxy, triphenylsilyloxy). These substituents may be further substituted by, for example, aforementioned substituents on the carbon atom.

$M^{11}$ represents a metal ion or a boron ion, each of which may further have a ligand(s), $M^{11}$ is preferably a metal ion that may further have a ligand(s), and more preferably a metal ion having no additional ligand. The metal ion is not particularly limited, but divalent or trivalent metal ions are preferable. As the divalent or trivalent metal ions, are preferable cobalt, magnesium, zinc, palladium, nickel, copper, platinum, lead, aluminum, iridium, europium, rhenium, rhodium and ruthenium ions. Of these, are more preferable cobalt, magnesium, zinc, palladium, nickel, copper, platinum and lead ions, with copper and platinum ions being further preferable. A platinum ion is particular preferable. When $n^{11}$ is 1, $M^{11}$ may or may not bond to an atom(s) being contained in $Q^{11}$, but it is preferable that $M^{11}$ bonds to the atom(s).

The aforementioned (additional) ligand that may be further opposed by $M^{11}$, is not particularly restricted, but it is preferably a monodentate or bidentate ligand, and more preferably a bidentate ligand. The coordinating atom is not particularly restricted, but it is preferably oxygen, sulfur, nitrogen, carbon and phosphorus atoms, more preferably oxygen, nitrogen and carbon atoms, and furthermore preferably oxygen and nitrogen atoms.

$n^{11}$ is preferably 0 or 1, more preferably 1.

The compounds represented by formula (1) are preferably those represented by formula (2) or (3), or their tautomers (those represented by formula (2) or their tautomers are more preferable); furthermore preferably the compounds represented by formula (4) or (5), or their tautomers (those represented by formula (4) or their tautomers are more preferable).

Further, as the compounds represented by formula (1), those represented by formula (11) or (15) are also preferable. As the compound represented by formula (11), there are preferably illustrated a compound represented by formula (12) or a tautomer thereof, a compound represented by formula (13) or a tautomer thereof, and a compound represented by formula (14) or a tautomer thereof; more preferably a compound represented by formula (12) or a tautomer thereof, and a compound represented by formula (13) or a tautomer thereof; and furthermore preferably a compound represented by formula (12) or a tautomer thereof.

As the compound represented by formulae (15), there are preferably illustrated a compound represented by formula (16) or a tautomer thereof, a compound represented by formula (17) or a tautomer thereof, and a compound represented by formula (18) or a tautomer thereof; more preferably a compound represented by formula (16) or a tautomer thereof, and a compound represented by formula (17) or a tautomer thereof; and furthermore preferably a compound represented by formula (16) or a tautomer thereof.

Next, the compound represented by formula (2) will be described.

$Z^{21}$, $Z^{22}$, $Z^{23}$, $Z^{24}$, $Z^{25}$, $Z^{26}$ and $M^{21}$ have the same meanings as those of the aforementioned $Z^{11}$, $Z^{12}$, $Z^{13}$, $Z^{11}$, $Z^{12}$, $Z^{13}$ and $M^{11}$, respectively, with the same preferable ranges.

$Q^{21}$ and $Q^{22}$ each represent a group for forming nitrogen-containing hetero ring. The nitrogen-containing hetero rings formed by $Q^{21}$ or $Q^{22}$ are not particularly limited, but are preferably a pyrrole ring, an imidazole ring, a triazole ring, a condensed ring containing at least one of these rings (for example, benzopyrrole), and a tautomer thereof (for example, as described below, in formula (4), the nitrogen-containing 5-membered rings having $R^{43}$, $R^{44}$, $R^{45}$ and $R^{46}$ are defined to be a tautomer of pyrrole), more preferably a pyrrole ring and a condensed ring containing a pyrrole ring (for example, benzopyrrole).

$X^{21}$, $X^{22}$, $X^{23}$ and $X^{24}$ each represent a substituted or unsubstituted carbon atom or nitrogen atom, preferably an unsubstituted carbon atom or nitrogen atom, and more preferably an unsubstituted nitrogen atom.

Next, the compound represented by formula (3) will be described.

$Q^{31}$, $Q^{32}$, $Z^{31}$, $Z^{32}$, $Z^{33}$, $Z^{34}$, $Z^{35}$, $Z^{36}$, $X^{31}$, $X^{32}$, $X^{33}$, and $X^{34}$ have the same meanings as those of the aforementioned $Q^{21}$, $Q^{22}$, $Z^{21}$, $Z^{22}$, $Z^{23}$, $Z^{24}$, $Z^{25}$, $Z^{26}$, $X^{21}$, $X^{22}$, $X^{23}$, and $X^{24}$ in formula (2), respectively, with the same preferable ranges.

$R^{31}$ and $R^{32}$ each represent a hydrogen atom or a substituent, with the hydrogen atom being preferable. As the substituent, there are illustrated, for example, an alkyl group, an alkenyl group, an aryl group, a hetero aryl group, an acyl group (e.g., acetyl, benzoyl, trifluoroacetyl) and a sulfonyl group (e.g., methanesulfonyl, pentafluorobenzenesulfonyl), that are exemplified as examples of the substituent on the carbon atom, when $Z^{11}$, $Z^{12}$ or $Z^{13}$ in the aforementioned formula (1) is a carbon atom. These substituents each may further have a substituent(s) (for example, any of the aforementioned substituents on the carbon atom).

Next, the compound represented by formula (4) will be described.

$Z^{41}$, $Z^{42}$, $Z^{43}$, $Z^{44}$, $Z^{45}$, $Z^{46}$, $X^{41}$, $X^{42}$, $X^{43}$, $X^{44}$ and $M^{41}$ have the same meanings as those of the aforementioned $Z^{21}$, $Z^{22}$, $Z^{23}$, $Z^{24}$, $Z^{25}$, $Z^{26}$, $X^{21}$, $X^{22}$, $X^{23}$, $X^{24}$, and $M^{21}$ in formula (2), respectively, with the same preferable ranges.

$R^{43}$, $R^{44}$, $R^{45}$ and $R^{46}$ each represent a hydrogen atom or a substituent. As the substituent, there can be mentioned groups that are exemplified as the substituent on the carbon atom with respect to $Z^{11}$ or $Z^{12}$ in the aforementioned formula (1).

$R^{43}$, $R^{44}$, $R^{45}$ and $R^{46}$ each are preferably a hydrogen atom, or an alkyl group or an aryl group that are exemplified as the substituent on $Z^{11}$ or $Z^{12}$ in the aforementioned formula (1), or a group that forms a ring structure (e.g., a benzene-condensed ring, a pyridine-condensed ring) when $R^{43}$ and $R^{44}$ or $R^{45}$ and $R^{46}$ bond to each other; more preferably an alkyl group, an aryl group, or a group that forms a ring structure (e.g., a benzene-condensed ring, a pyridine-condensed ring) when $R^{43}$ and $R^{44}$ or $R^{45}$ and $R^{46}$ bond to each other; and furthermore preferably a group that forms a ring structure (e.g., a benzene-condensed ring, a pyridine-condensed ring) when $R^{43}$ and $R^{44}$ or $R^{45}$ and $R^{46}$ bond to each other.

Next, the compound represented by formula (5) will be described.

$R^{51}$, $R^{52}$, $R^{53}$, $R^{54}$, $R^{55}$, $R^{56}$, $Z^{51}$, $Z^{52}$, $Z^{53}$, $Z^{54}$, $Z^{55}$, $Z^{56}$, $X^{51}$, $X^{52}$, $X^{53}$, and $X^{54}$ have the same meanings as those of the aforementioned $R^{31}$, $R^{32}$, $R^{43}$, $R^{44}$, $R^{45}$, $R^{46}$, $Z^{41}$, $Z^{42}$, $Z^{43}$, $Z^{44}$, $Z^{45}$, $Z^{46}$, $X^{41}$, $X^{41}$, $X^{42}$, $X^{43}$, and $X^{44}$ in formulas (3) and (4), respectively, with the same preferable ranges.

Next, the compound represented by formula (6) will be described.

$R^{63}$, $R^{64}$, $R^{65}$, $R^{66}$, $Z^{61}$, $Z^{62}$, $Z^{63}$, $Z^{64}$, $Z^{65}$, $Z^{66}$, $X^{61}$, $X^{62}$, $X^{63}$, and $X^{64}$ have the same meanings as those of the aforementioned $R^{43}$, $R^{44}$, $R^{45}$, $R^{46}$, $Z^{41}$, $Z^{42}$, $Z^{43}$, $Z^{44}$, $Z^{45}$, $Z^{46}$, $X^{41}$, $X^{42}$, $X^{43}$, and $X^{44}$ in formula (4), respectively, with the same preferable ranges.

Next, the compound represented by formula (11) will be described.

$Z^{101}$, $Z^{102}$ and $Z^{103}$ each represent a substituted or unsubstituted carbon atom or nitrogen atom. At least one of $Z^{101}$, $Z^{102}$ and $Z^{103}$ is preferably a nitrogen atom.

$L^{101}$, $L^{102}$, $L^{103}$ and $L^{104}$ each represent a single bond or a linking group. The linking group is not particularly restricted. Examples of the linking group include a carbonyl-linking group, an alkylene group, an alkenylene group, an arylene group, a hetero arylene group, a nitrogen-containing hetero ring-linking group, an oxygen atom-linking group, an amino-linking group, an imino-linking group, and a combination of at least two groups selected from these linking groups.

As the $L^{101}$, $L^{102}$, $L^{103}$ and $L^{104}$, there are preferably illustrated a single bond, an alkylene group, an alkenylene group, an oxygen atom-linking group, an amino-linking group, and an imino-linking group, more preferably a single bond, an alkylene linking group, an alkenylene linking group, and an imino-linking group, and furthermore preferably a single bond and an alkylene linking group.

$Q^{101}$ and $Q^{103}$ each represent a group containing a carbon, nitrogen, phosphorus, oxygen or sulfur atom as a coordinating atom to $M^{101}$ respectively.

As the group containing a carbon atom as the coordinating atom, there are preferably illustrated an aryl group, a 5-membered hetero aryl group, and a 6-membered hetero aryl group, each containing a carbon atom as the coordinating atom, more preferably an aryl group, a 5-membered nitrogen-containing hetero aryl group, and a 6-membered nitrogen-containing hetero aryl group, each containing a carbon atom as the coordinating atom, and furthermore preferably an aryl group containing a carbon atom as the coordinating atom.

As the group containing a nitrogen atom as the coordinating atom, there are preferably illustrated a 5-membered nitrogen-containing hetero aryl group, and a 6-membered nitrogen-containing hetero aryl group, each containing a nitrogen atom as the coordinating atom, and more preferably a 6-membered nitrogen-containing hetero aryl group containing a nitrogen atom as the coordinating atom.

As the group containing a phosphorus atom as the coordinating atom, there are preferably illustrated an alkylphosphine group, an arylphosphine group, an alkoxyphosphine group, an aryloxyphosphine group, a hetero aryloxyphosphine group, a phosphinine group, and a phosphole group, each containing a phosphorus atom as the coordinating atom, and more preferably an alkylphosphine group, and an arylphosphine group, each containing a phosphorus atom as the coordinating atom.

As the group containing a oxygen atom as the coordinating atom, there are preferably illustrated an oxy group, and a carboxyl group containing an oxygen atom as the coordinating atom, and more preferably an oxy group.

As the group containing a sulfur atom as the coordinating atom, there are preferably illustrated a sulfido group, a thiophene group, and a thiazole group, and more preferably a thiophene group.

$Q^{101}$ and $Q^{103}$ each preferably represent a group containing a carbon, nitrogen, or oxygen atom as a coordinating atom to $M^{101}$ respectively; more preferably a group containing a carbon or nitrogen atom as the coordinating atom; and further preferably a group containing a carbon atom as the coordinating atom.

$Q^{102}$ represents a group containing a nitrogen, phosphorus, oxygen or sulfur atom as a coordinating atom to $M^{101}$ respectively. The group containing a nitrogen atom as the coordinating atom is more preferable as $Q^{102}$.

$M^{101}$ has the same meaning as that of the aforementioned $M^{11}$, with the same preferable range.

Next, the compound represented by formula (15) will be described.

$Z^{501}$, $Z^{502}$, $Z^{503}$, $L^{501}$, $L^{502}$, $L^{503}$, $L^{504}$, $Q^{501}$, $Q^{502}$, $Q^{503}$, and $M^{501}$ have the same meanings as those of the aforementioned $Z^{101}$, $Z^{102}$, $Z^{103}$, $L^{101}$, $L^{102}$, $L^{103}$, $L^{104}$, $Q^{101}$, $Q^{103}$, $Q^{102}$, and $M^{101}$, respectively, with the same preferable ranges.

Next, the compound represented by formula (12) will be described.

$Z^{201}$, $Z^{202}$, $Z^{203}$, $Z^{207}$, $Z^{208}$, $Z^{209}$, $L^{201}$, $L^{202}$, $L^{203}$, $L^{204}$, and $M^{201}$ have the same meanings as those of the aforementioned $Z^{101}$, $Z^{102}$, $Z^{103}$, $Z^{101}$, $Z^{102}$, $Z^{103}$, $L^{101}$, $L^{102}$, $L^{103}$, $L^{104}$, and $M^{101}$, respectively, with the same preferable ranges. $Z^{204}$, $Z^{205}$, $Z^{206}$, $Z^{210}$, $Z^{211}$ and $Z^{212}$ each represent a substituted or unsubstituted carbon atom or nitrogen atom, with a substituted or unsubstituted carbon atom being preferable.

A combination of $L^{201}$, $L^{202}$, $L^{203}$ and $L^{204}$ is preferably that $L^{201}$, $L^{202}$, $L^{203}$ and $L^{204}$ each are an alkylene group; and more preferably that $L^{201}$ and $L^{203}$ each are a single bond, and $L^{202}$ and $L^{204}$ each are an alkylene group. A combination of $Z^{204}$, $Z^{206}$, $Z^{210}$ and $Z^{212}$ is preferably that at least one of $Z^{204}$, $Z^{206}$, $Z^{210}$ and $Z^{212}$ is a carbon atom substituted with a fluorine atom; and more preferably that $Z^{204}$, $Z^{206}$, $Z^{210}$ and $Z^{212}$ each are a carbon atom substituted with a fluorine atom. It is preferable that $Z^{202}$ and $Z^{208}$ each independently are a carbon atom substituted with any of an alkyl group, alkoxy group or dialkylamino group.

Next, the compound represented by formula (13) will be described.

$Z^{301}$, $Z^{302}$, $Z^{303}$, $Z^{304}$, $Z^{305}$, $Z^{306}$, $Z^{307}$, $Z^{308}$, $Z^{309}$, $Z^{310}$, $L^{301}$, $L^{302}$, $L^{303}$, $L^{304}$, and $M^{301}$ have the same meanings as those of the aforementioned $Z^{201}$, $Z^{202}$, $Z^{203}$, $Z^{204}$, $Z^{206}$, $Z^{207}$, $Z^{208}$, $Z^{209}$, $Z^{210}$, $Z^{212}$, $L^{101}$, $L^{102}$, $L^{103}$, $L^{104}$, and $M^{101}$, respectively, with the same preferable ranges.

A combination of $L^{301}$, $L^{302}$, $L^{303}$ and $L^{304}$ is preferably that $L^{301}$, $L^{302}$, $L^{303}$ and $L^{304}$ each are an alkylene group; and more preferably that $L^{301}$ and $L^{303}$ each are a single bond, and $L^{302}$ and $L^{304}$ each are an alkylene group. A combination of $Z^{304}$, $Z^{305}$, $Z^{309}$ and $Z^{310}$ is preferably that at least two of $Z^{304}$, $Z^{305}$, $Z^{309}$ and $Z^{310}$ are each a nitrogen atom. It is preferable that $Z^{302}$ and $Z^{307}$ each independently are a carbon atom substituted with any of an alkyl group, alkoxy group or dialkylamino group.

Next, the compound represented by formula (14) will be described.

$Z^{401}$, $Z^{402}$, $Z^{403}$, $Z^{404}$, $Z^{405}$, $Z^{406}$, $Z^{407}$, $Z^{408}$, $Z^{409}$, $Z^{410}$, $Z^{411}$, $Z^{412}$, $L^{401}$, $L^{402}$, $L^{403}$, $L^{404}$, and $M^{401}$ have the same meanings as those of the aforementioned $Z^{201}$, $Z^{202}$, $Z^{203}$, $Z^{204}$, $Z^{205}$, $Z^{206}$, $Z^{207}$, $Z^{208}$, $Z^{209}$, $Z^{210}$, $Z^{211}$, $Z^{212}$, $L^{101}$, $L^{102}$, $L^{103}$, $L^{104}$, and $M^{101}$, respectively, with the same preferable ranges.

$X^{401}$ and $X^{402}$ each represent an oxygen atom, a substituted or unsubstituted nitrogen atom, or a sulfur atom, preferably an oxygen atom or a substituted nitrogen atom, and more preferably an oxygen atom.

A combination of $L^{401}$, $L^{402}$, $L^{403}$ and $L^{404}$ is preferably that $L^{401}$, $L^{402}$, $L^{403}$ and $L^{404}$ each are an alkylene group; and more preferably that $L^{401}$ and $L^{403}$ each are a single bond, and $L^{402}$ and $L^{404}$ each are an alkylene group. A combination of $Z^{404}$, $Z^{406}$, $Z^{410}$ and $Z^{412}$ is preferably that at least one of $Z^{404}$, $Z^{406}$, $Z^{410}$ and $Z^{412}$ is a carbon atom substituted with a fluorine atom; and more preferably that $Z^{404}$, $Z^{406}$, $Z^{410}$ and $Z^{412}$ each are a carbon atom substituted with a fluorine atom. It is preferable that $Z^{402}$ and $Z^{408}$ each independently are a carbon atom substituted with any of an alkyl group, alkoxy group or dialkylamino group.

Next, the compound represented by formula (16) will be described.

$Z^{601}$, $Z^{602}$, $Z^{603}$, $Z^{604}$, $Z^{605}$, $Z^{606}$, $Z^{607}$, $Z^{608}$, $Z^{609}$, $Z^{610}$, $Z^{611}$, $Z^{612}$, $L^{601}$, $L^{602}$, $L^{603}$, $L^{604}$, and $M^{601}$ have the same meanings as those of the aforementioned $Z^{201}$, $Z^{202}$, $Z^{203}$, $Z^{207}$, $Z^{208}$, $Z^{209}$, $Z^{204}$, $Z^{205}$, $Z^{206}$, $Z^{210}$, $Z^{211}$, $Z^{212}$, $L^{101}$, $L^{102}$, $L^{103}$, $L^{104}$, and $M^{101}$, respectively, with the same preferable ranges.

A combination of $L^{601}$, $L^{602}$, $L^{603}$ and $L^{604}$ is preferably that $L^{601}$, $L^{602}$, $L^{603}$ and $L^{604}$ each are an alkylene group; and more preferably that $L^{601}$ and $L^{603}$ each are a single bond, and $L^{602}$ and $L^{604}$ each are an alkylene group. A combination of $Z^{607}$, $Z^{609}$, $Z^{610}$ and $Z^{612}$ is preferably that at least one of $Z^{607}$, $Z^{609}$, $Z^{610}$ and $Z^{612}$ is a carbon atom substituted with a fluorine atom; and more preferably that $Z^{607}$, $Z^{609}$, $Z^{610}$ and $Z^{612}$ each are a carbon atom substituted with a fluorine atom. It is preferable that $Z^{602}$ and $Z^{605}$ each independently are a carbon atom substituted with any of an alkyl group, alkoxy group or dialkylamino group.

Next, the compound represented by formula (17) will be described.

$Z^{701}$, $Z^{702}$, $Z^{703}$, $Z^{704}$, $Z^{705}$, $Z^{706}$, $Z^{707}$, $Z^{708}$, $Z^{709}$, $Z^{710}$, $L^{701}$, $L^{702}$, $L^{703}$, $L^{704}$, and $M^{701}$ have the same meanings as those of the aforementioned $Z^{201}$, $Z^{202}$, $Z^{203}$, $Z^{207}$, $Z^{208}$, $Z^{209}$, $Z^{204}$, $Z^{206}$, $Z^{210}$, $Z^{212}$, $L^{101}$, $L^{102}$, $L^{103}$, $L^{104}$, and $M^{101}$, respectively, with the same preferable ranges.

A combination of $L^{701}$, $L^{702}$, $L^{703}$ and $L^{704}$ is preferably that $L^{701}$, $L^{702}$, $L^{703}$ and $L^{704}$ each are an alkylene group; and more preferably that $L^{701}$ and $L^{703}$ each are a single bond, and $L^{702}$ and $L^{704}$ each are an alkylene group. A combination of $Z^{707}$, $Z^{708}$, $Z^{709}$ and $Z^{710}$ is preferably that at least two of $Z^{707}$, $Z^{708}$, $Z^{709}$ and $Z^{710}$ are each a nitrogen atom. It is preferable that $Z^{702}$ and $Z^{705}$ each independently are a carbon atom substituted with any of an alkyl, group, alkoxy group or dialkylamino group.

Next, the compound represented by formula (18) will be described.

$Z^{801}$, $Z^{802}$, $Z^{803}$, $Z^{804}$, $Z^{805}$, $Z^{806}$, $Z^{807}$, $Z^{808}$, $Z^{809}$, $Z^{810}$, $Z^{811}$, $Z^{812}$, $L^{801}$, $L^{802}$, $L^{803}$, $L^{804}$, $M^{801}$, $X^{801}$ and $X^{802}$ have the same meanings as those of the aforementioned $Z^{201}$, $Z^{202}$, $Z^{203}$, $Z^{207}$, $Z^{208}$, $Z^{209}$, $Z^{204}$, $Z^{205}$, $Z^{206}$, $Z^{210}$, $Z^{211}$, $Z^{212}$, $L^{101}$, $L^{102}$, $L^{103}$, $L^{104}$, $M^{101}$, $X^{401}$ and $X^{402}$ respectively, with the same preferable ranges.

A combination of $L^{801}$, $L^{802}$, $L^{803}$ and $L^{804}$ is preferably that $L^{801}$, $L^{802}$, $L^{803}$ and $L^{804}$ each are an alkylene group; and more preferably that $L^{801}$ and $L^{803}$ each are a single bond, and $L^{802}$ and $L^{804}$ each are an alkylene group. A combination of $Z^{807}$, $Z^{809}$, $Z^{810}$ and $Z^{812}$ is preferably that at least one of $Z^{807}$, $Z^{809}$, $Z^{810}$ and $Z^{812}$ is a carbon atom substituted with a fluorine atom; and more preferably that $Z^{807}$, $Z^{809}$, $Z^{810}$ and $Z^{812}$ each are a carbon atom substituted with a fluorine atom. It is preferable that $Z^{802}$ and $Z^{805}$ each independently are a carbon atom substituted with any of an alkyl group, alkoxy group or dialkylamino group.

The compound of the present invention may be a low molecular compound, or may be an oligomer compound or a polymer compound having a weight-average molecular weight calculated in terms of polystyrene preferably in the range of 1,000 to 5,000,000, more preferably in the range of 2,000 to 1,000,000, and furthermore preferably in the range of 3,000 to 100,000. With respect to the polymer compound, the structure represented, for example, by formula (1) may be contained in a main chain of the polymer, or in a side chain of the polymer. Further, the polymer compound may be a homopolymer or a copolymer. The compound of the present invention is preferably a low molecular compound.

Specific examples of the compound of the present invention are shown below, but the present invention is not limited to these compounds.

Compound (1)

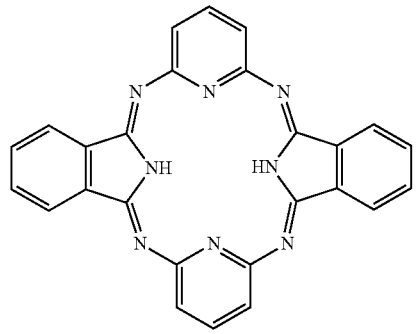

Compound (2)

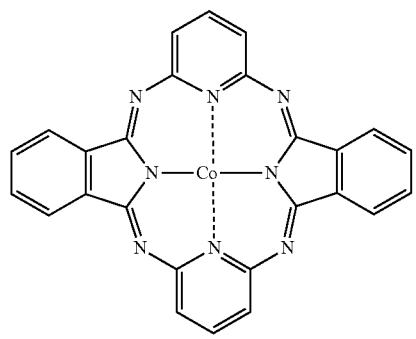

Compound (3)

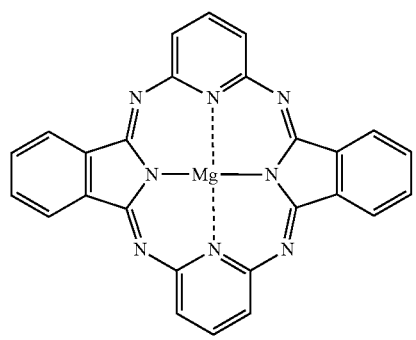

Compound (4)

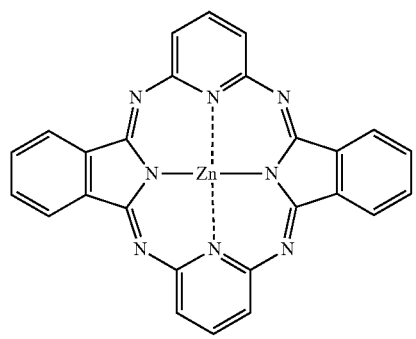

-continued
Compound (5)
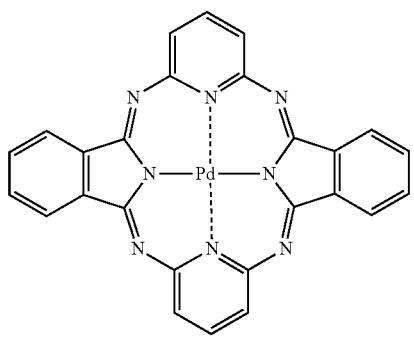
Compound (9)
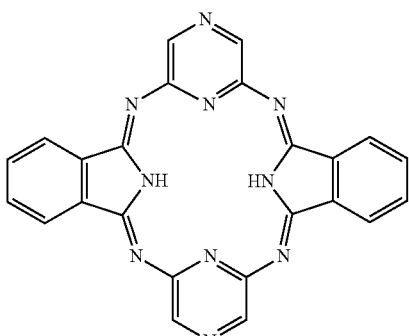
Compound (6)
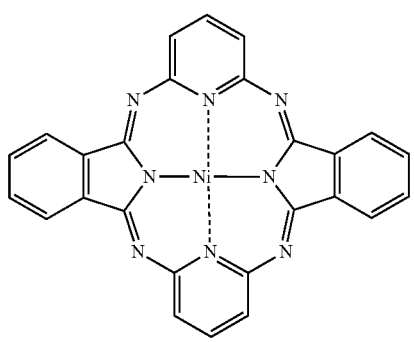
Compound (10)
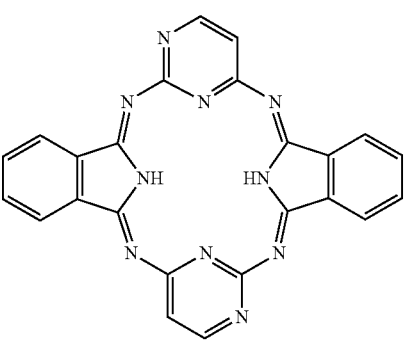
Compound (7)
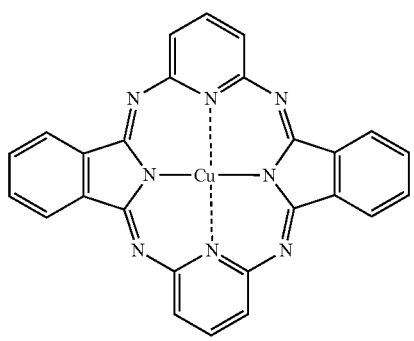
Compound (11)
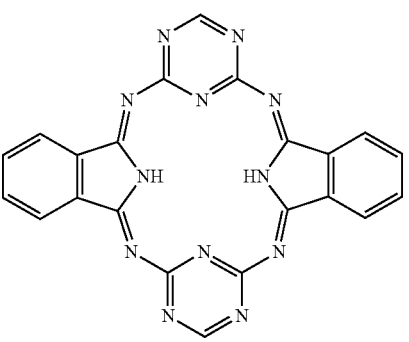
Compound (8)
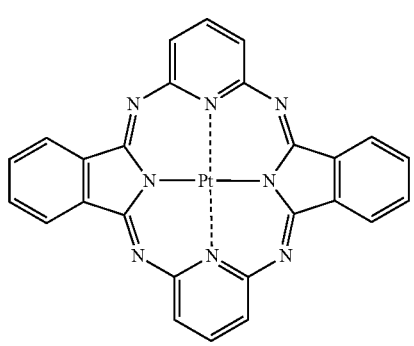
Compound (12)
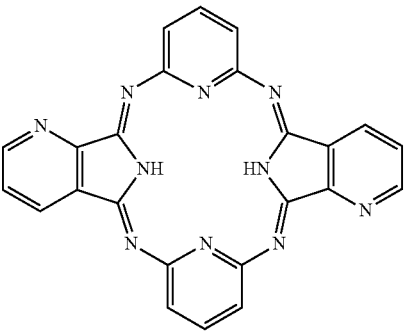

-continued
Compound (13)
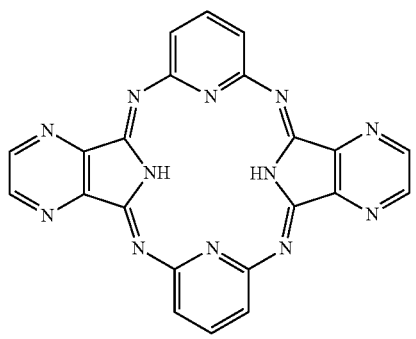
Compound (14)
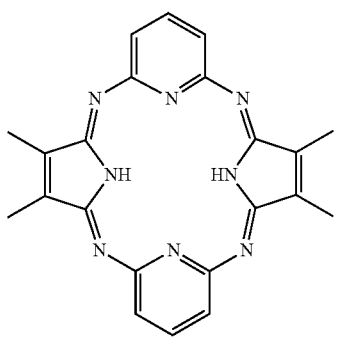
Compound (15)
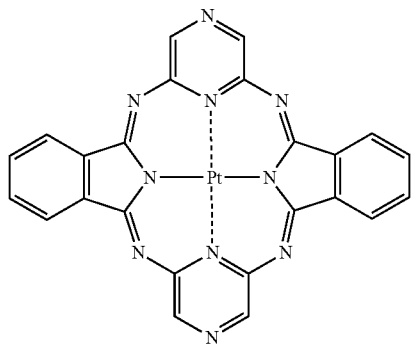
Compound (16)
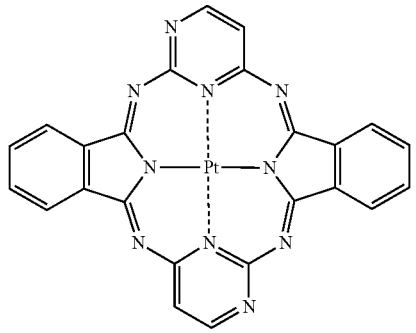
Compound (17)
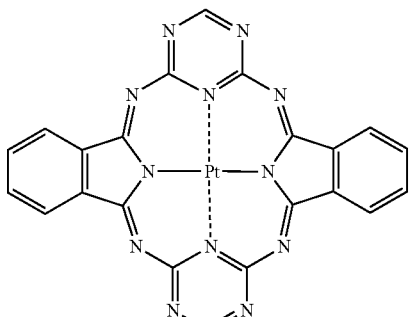
Compound (18)
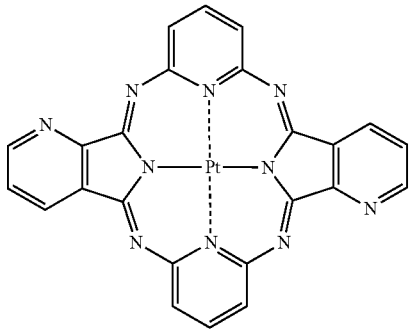
Compound (19)
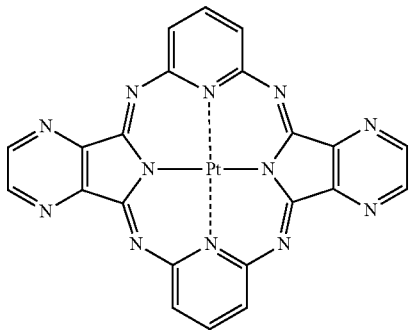
Compound (20)
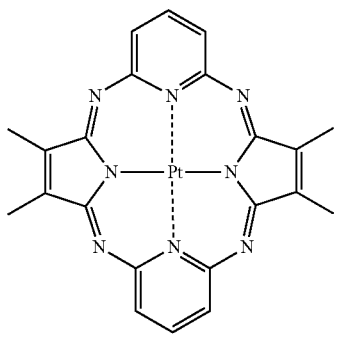

Compound (21)
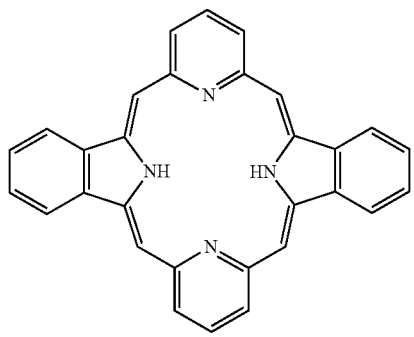
Compound (22)
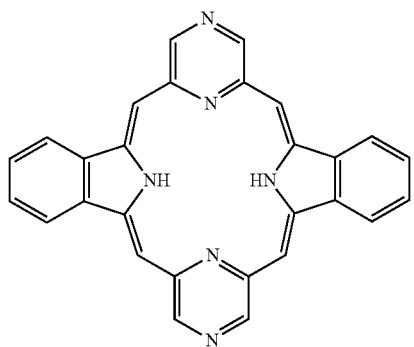
Compound (23)
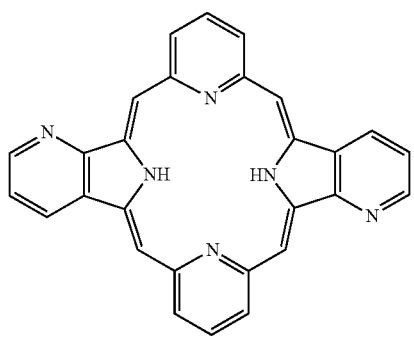
Compound (24)
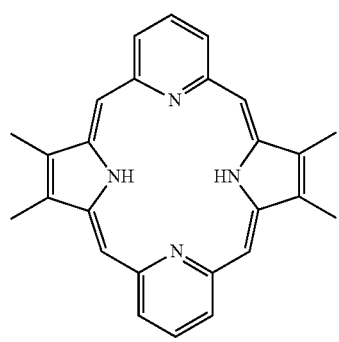
Compound (25)
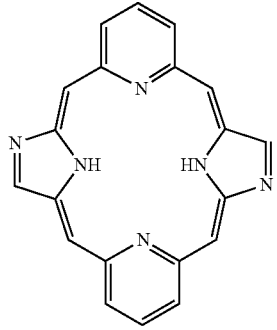
Compound (26)
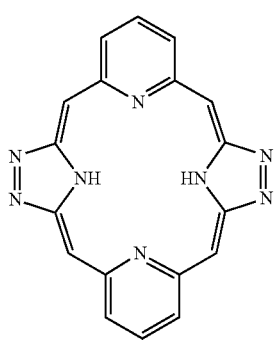
Compound (27)
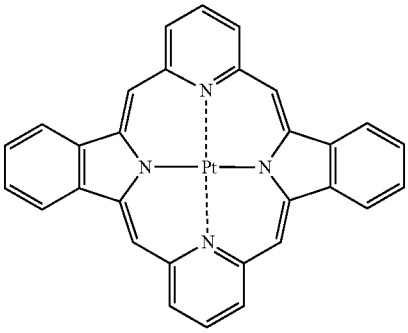
Compound (28)
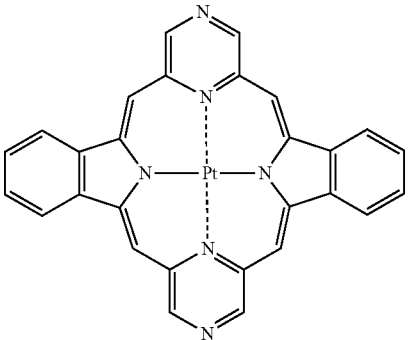

Compound (29)
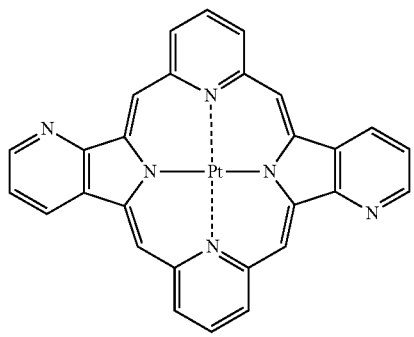
Compound (30)
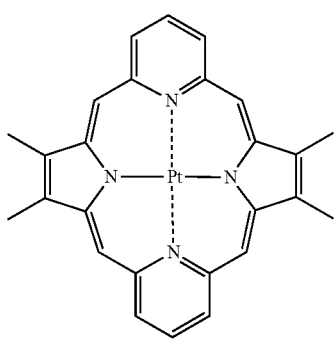
Compound (31)
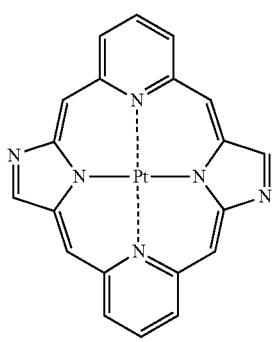
Compound (32)
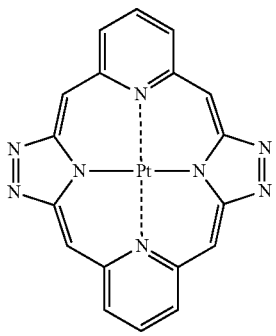
Compound (33)
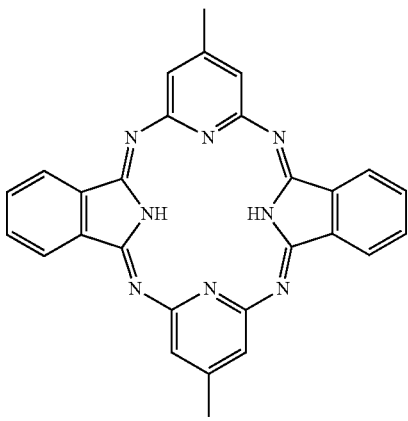
Compound (34)
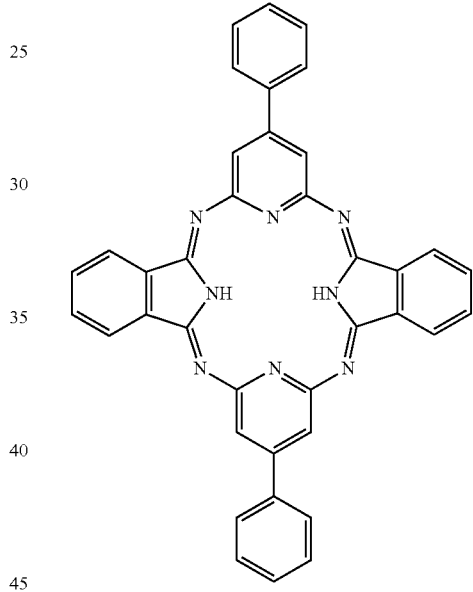
Compound (35)
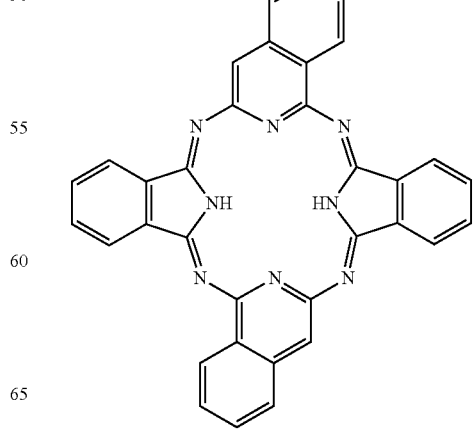

Compound (36)
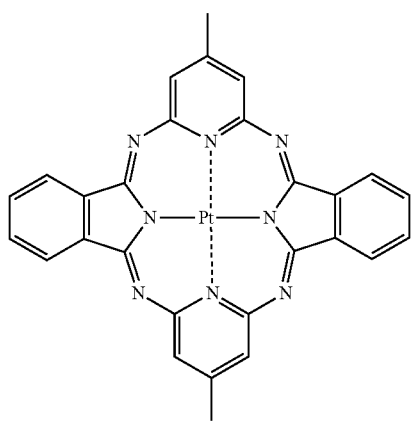
Compound (37)
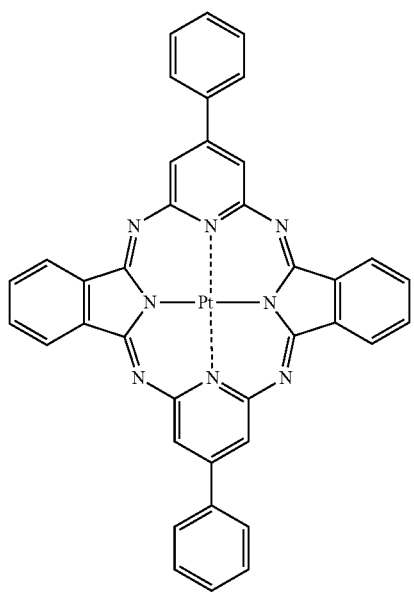
Compound (38)
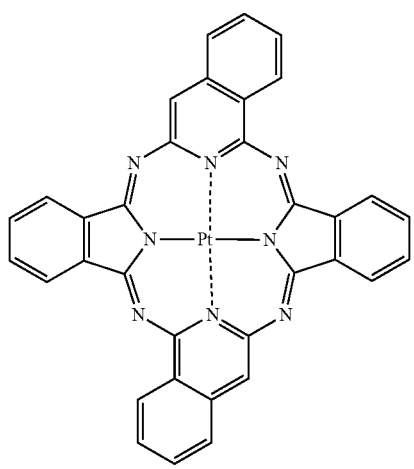
Compound (39)
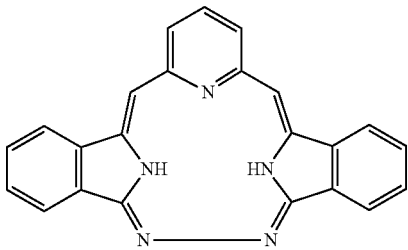
Compound (40)
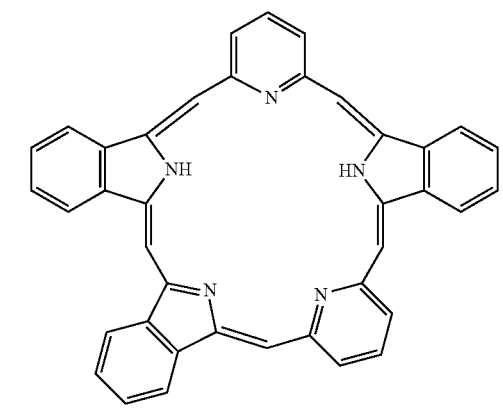
Compound (41)
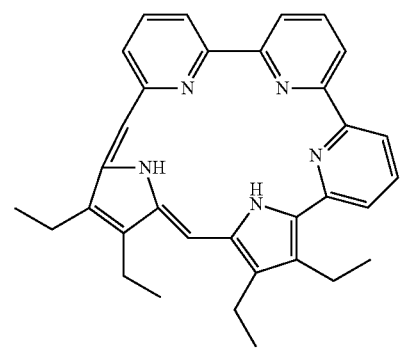
Compound (42)
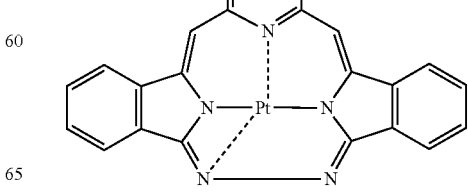

Compound (43)
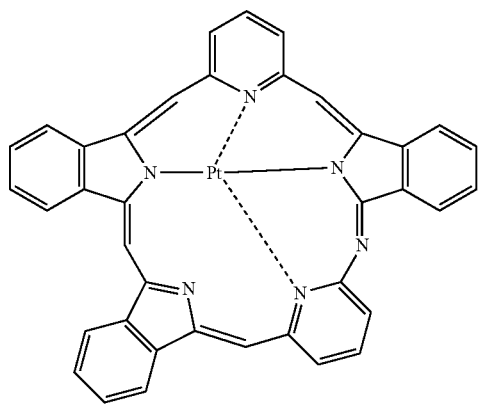
Compound (44)
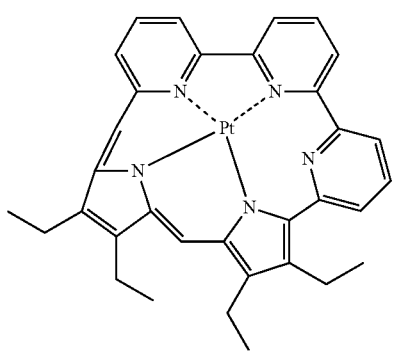
Compound (45)
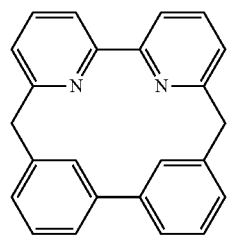
Compound (46)
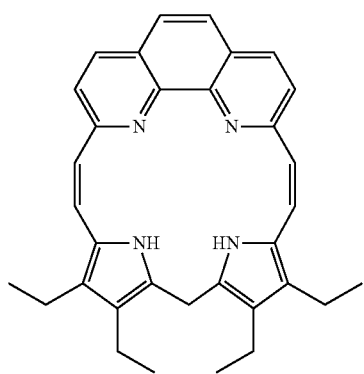
Compound (47)
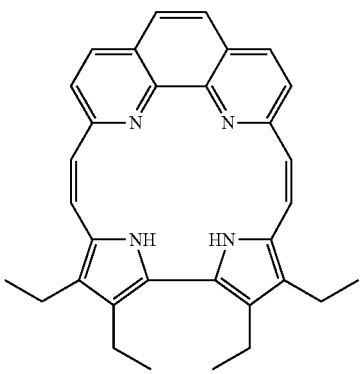
Compound (48)
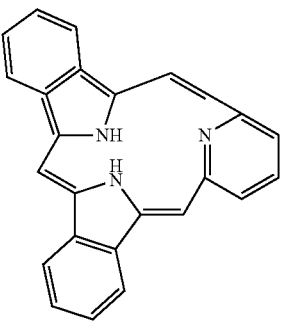
Compound (49)
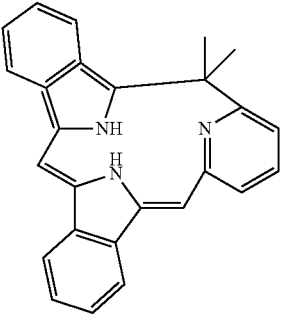
Compound (50)
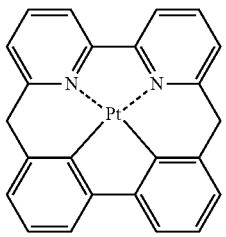
Compound (51)
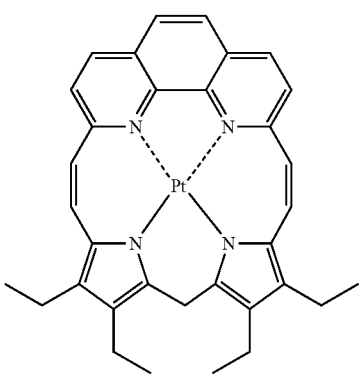

Compound (52)
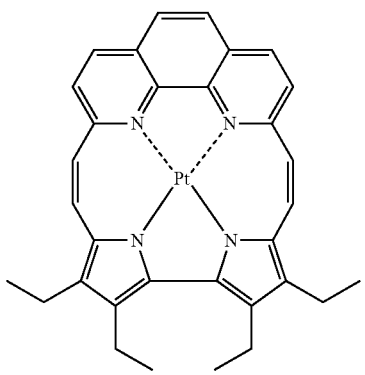
Compound (53)
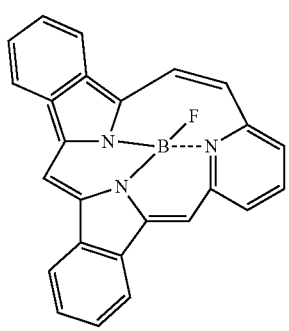
Compound (54)
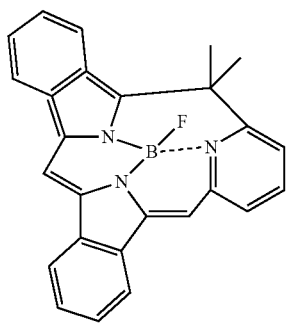
Compound (55)
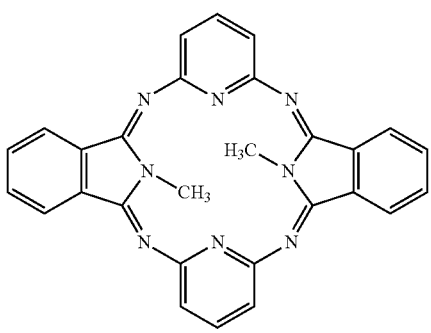
Compound (56)
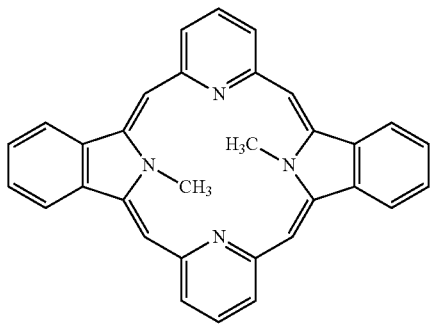
Compound (57)
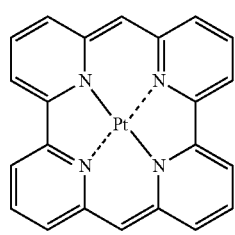
Compound (58)
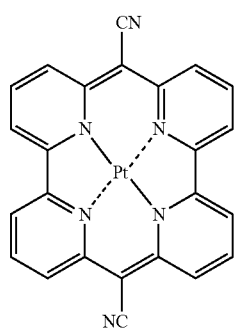
Compound (59)
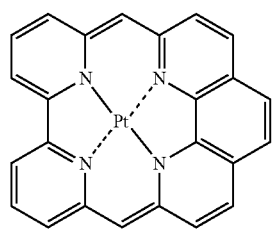
Compound (60)

Compound (61)
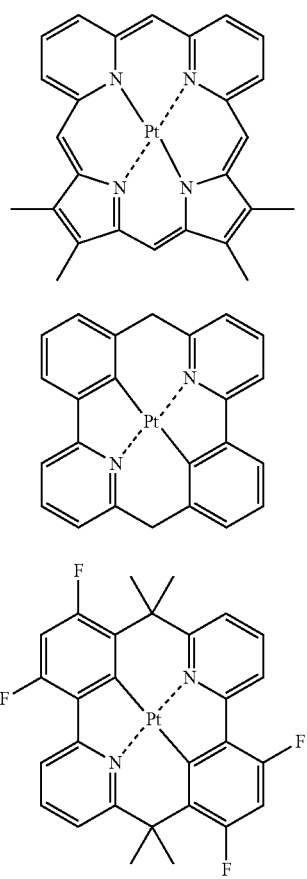
Compound (62)
Compound (63)
Compound (64)
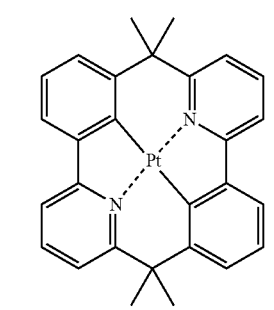
Compound (65)
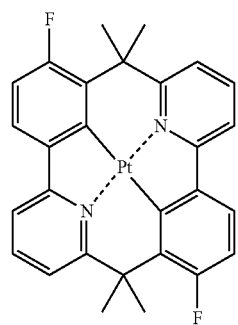
Compound (66)
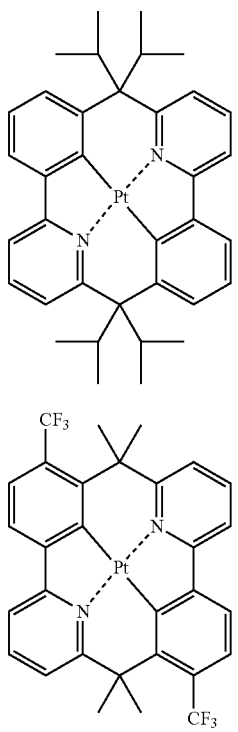
Compound (67)
Compound (68)
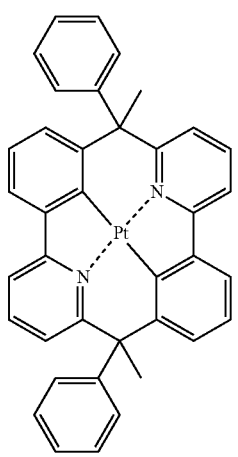
Compound (69)
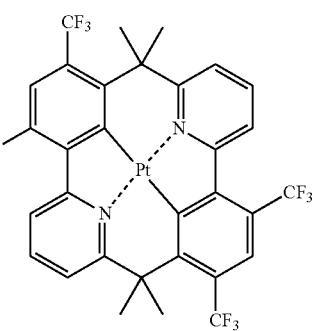

Compound (70)
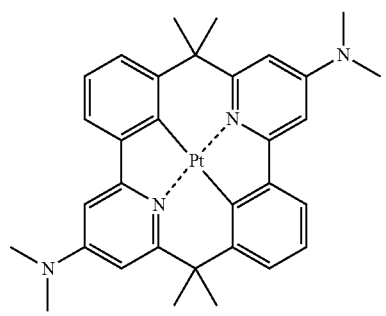
Compound (71)
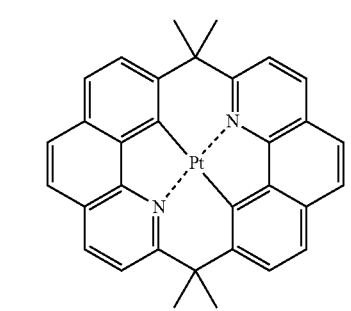
Compound (72)
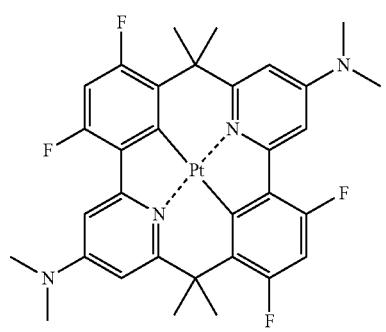
Compound (73)
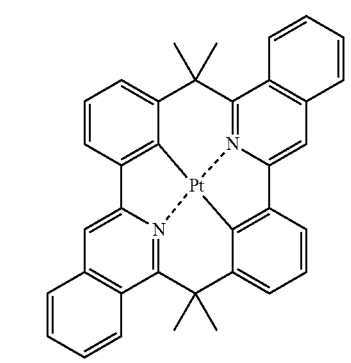
Compound (74)
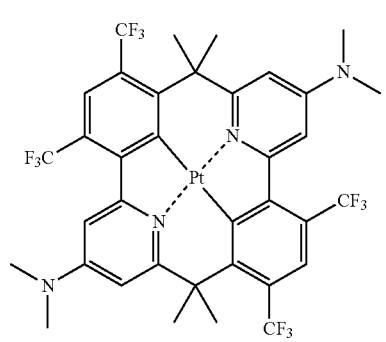
Compound (75)
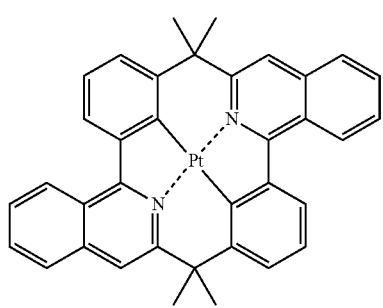
Compound (76)
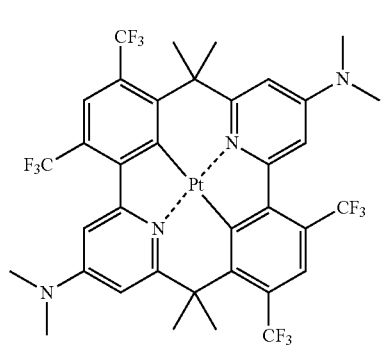
Compound (77)
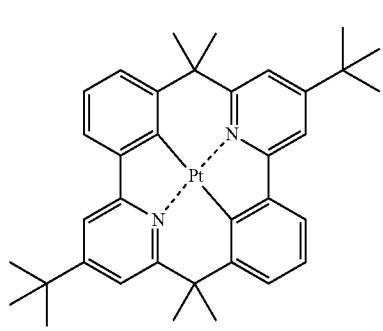
Compound (78)
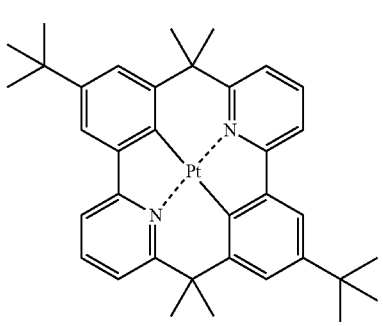
Compound (79)
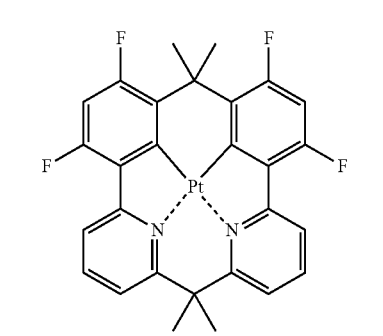

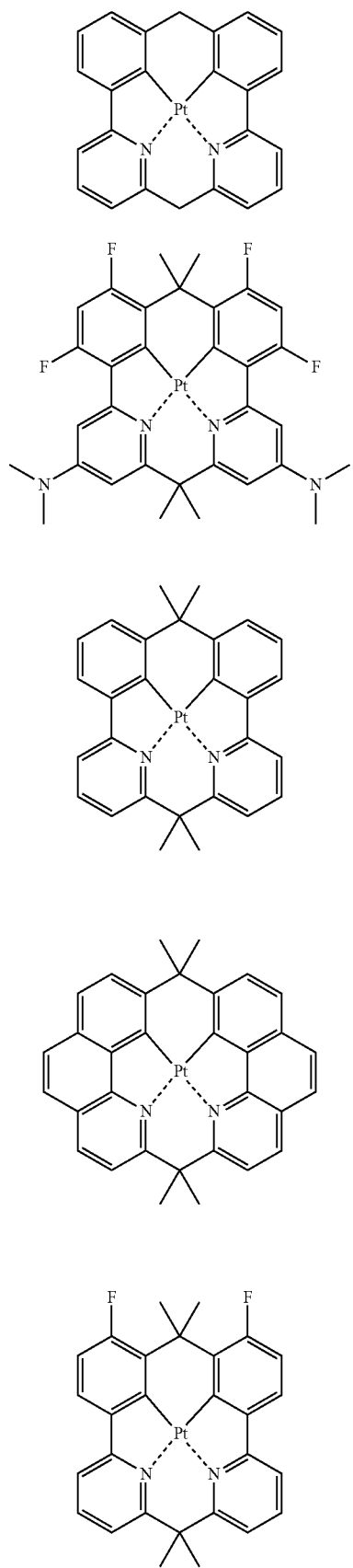
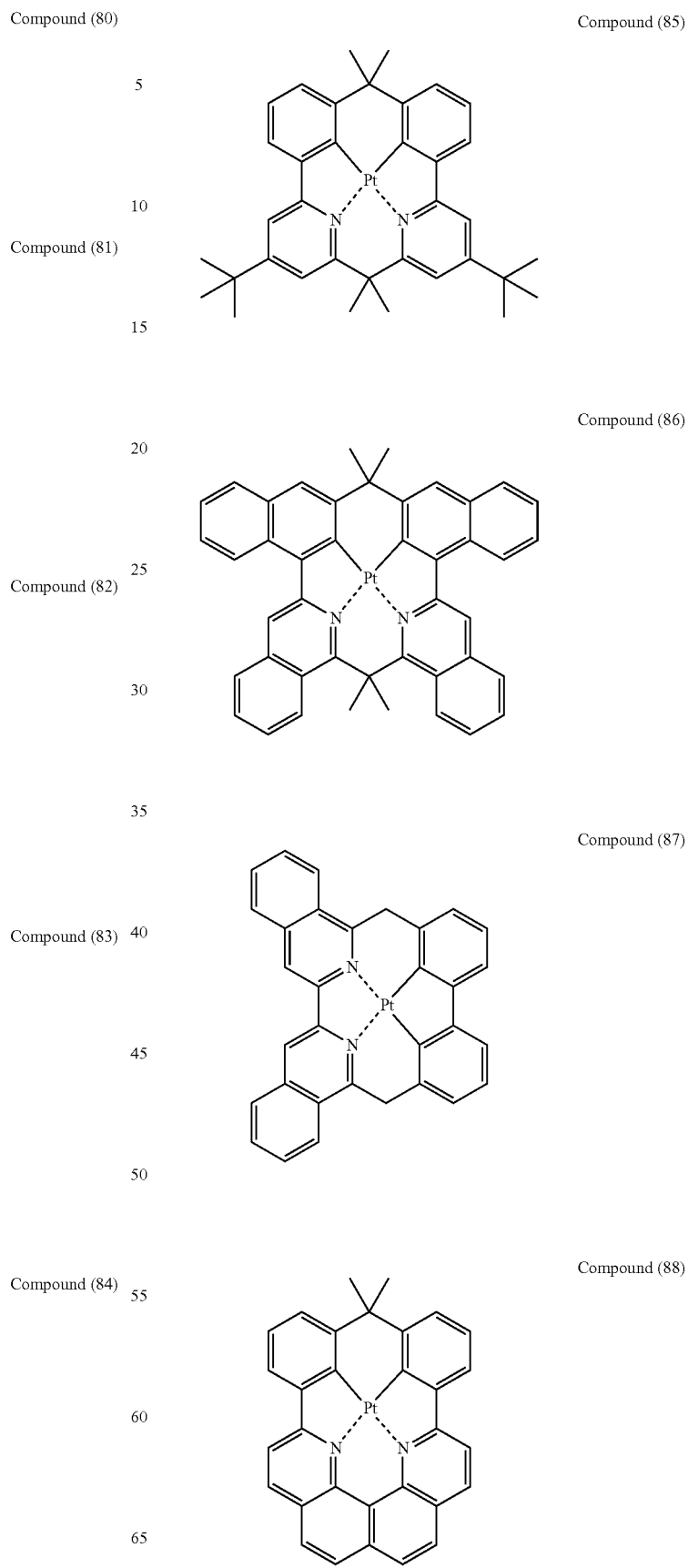

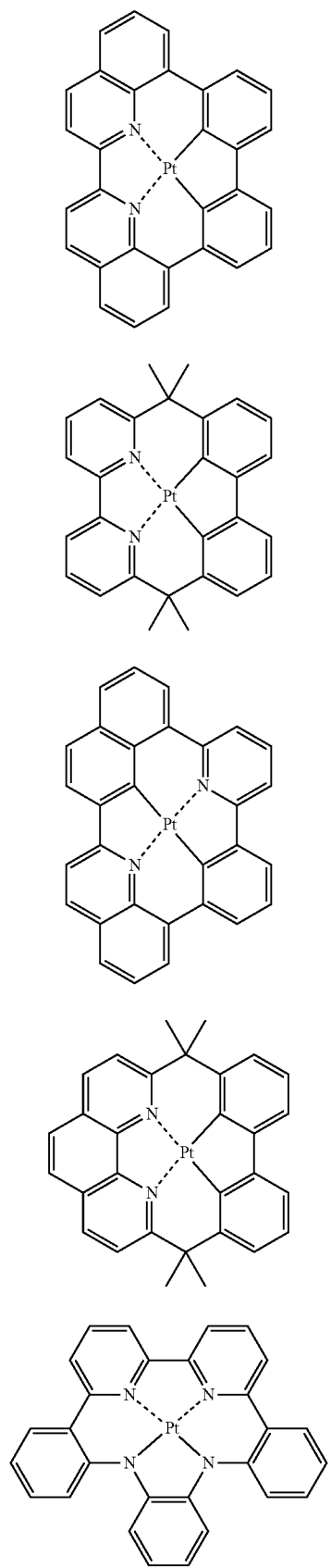
Compound (89)
Compound (90)
Compound (91)
Compound (92)
Compound (93)
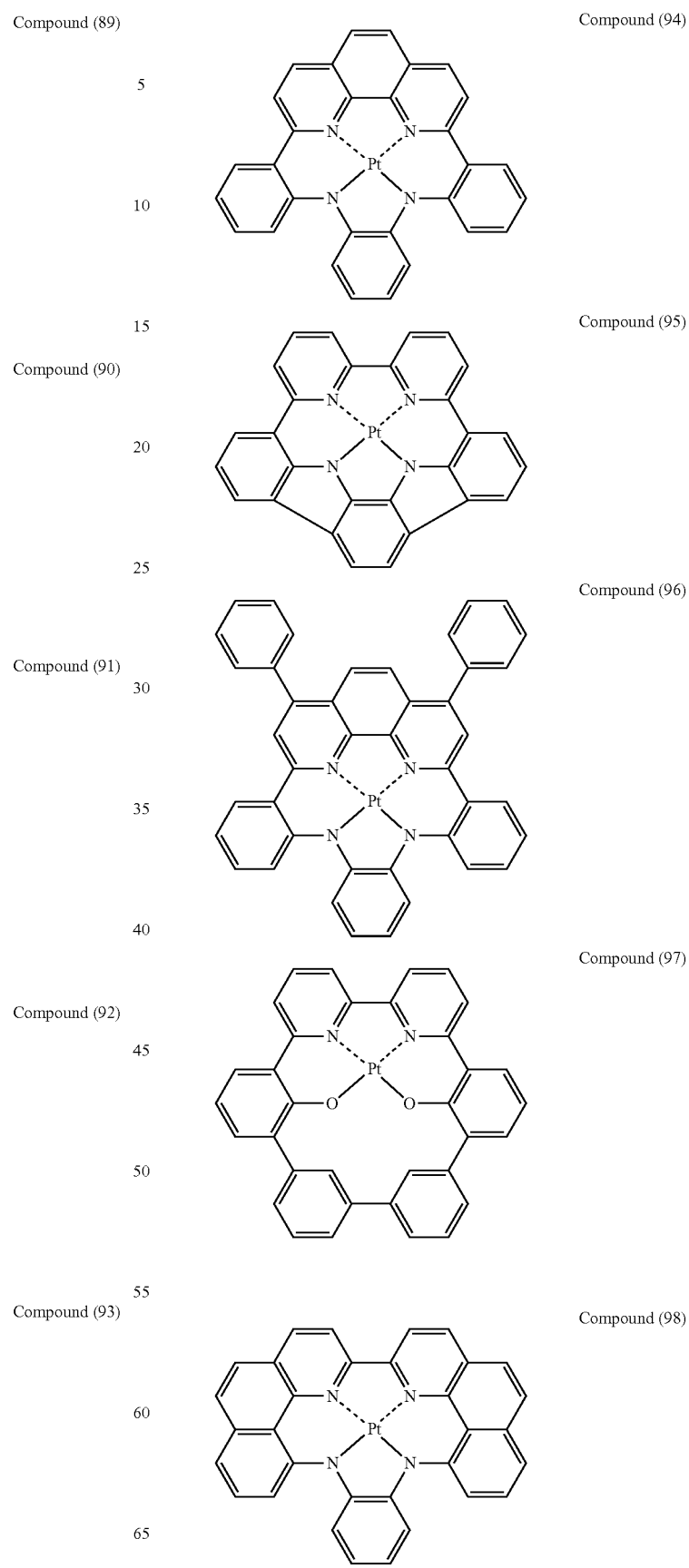
Compound (94)
Compound (95)
Compound (96)
Compound (97)
Compound (98)

Compound (99)
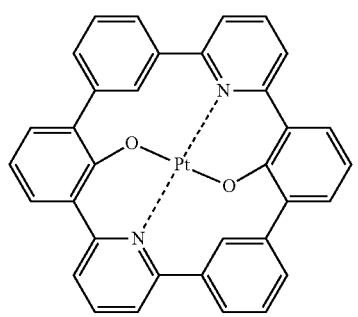
Compound (100)
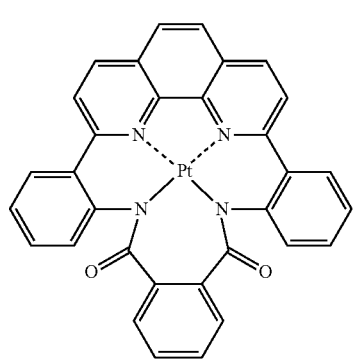
Compound (101)
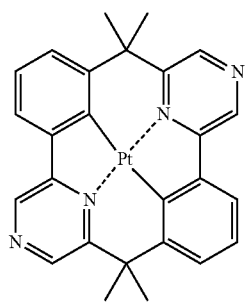
Compound (102)
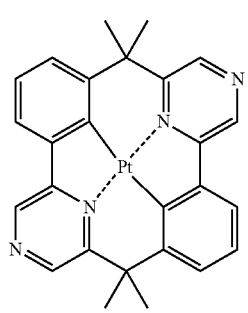
Compound (103)
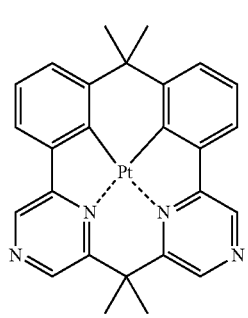
Compound (104)
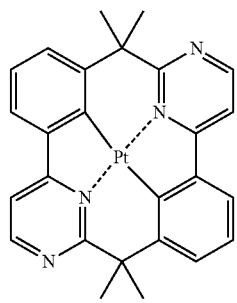
Compound (105)
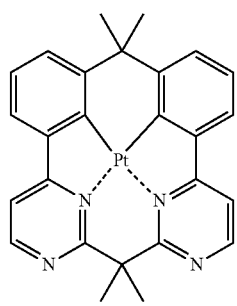
Compound (106)
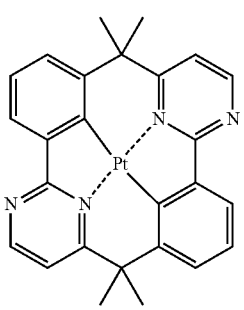
Compound (107)
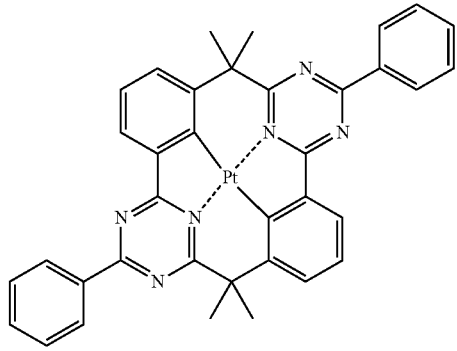
Compound (108)
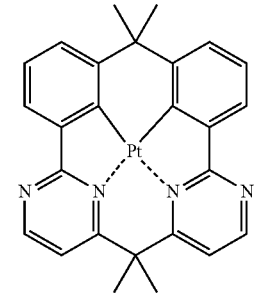

Compound (109)
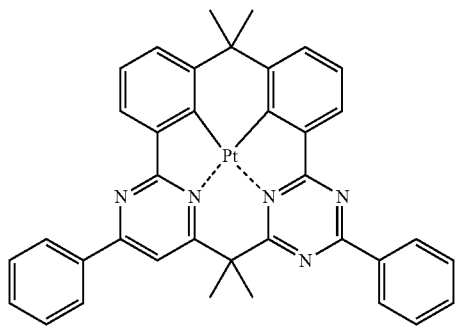
Compound (110)
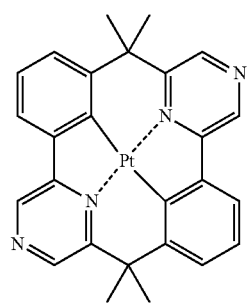
Compound (111)
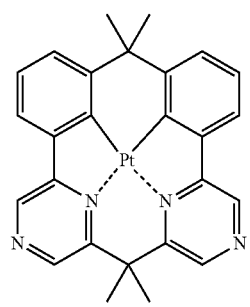
Compound (112)
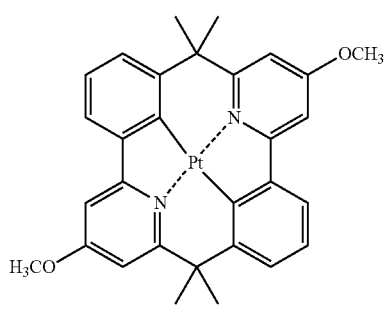
Compound (113)
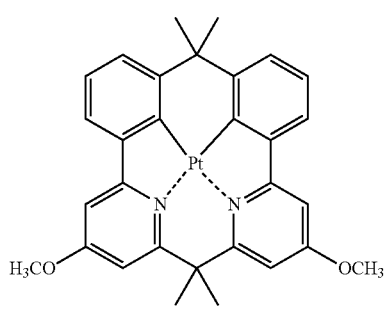
Compound (114)
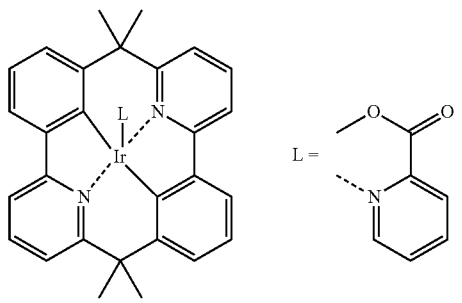
Compound (115)
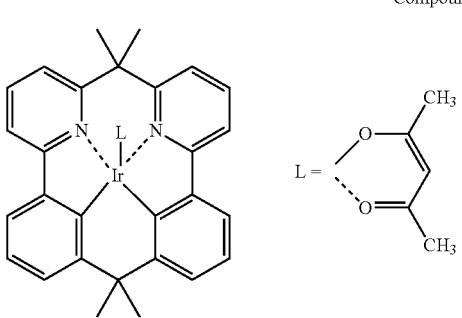
Compound (116)
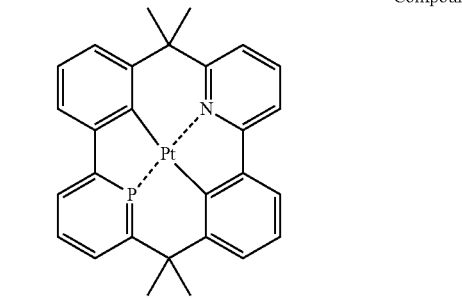
Compound (117)
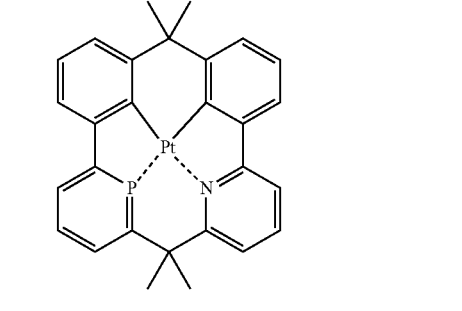
Compound (118)
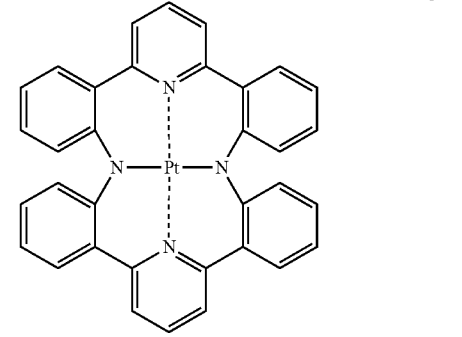

Compound (119)
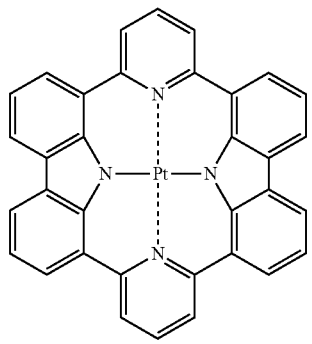
Compound (120)
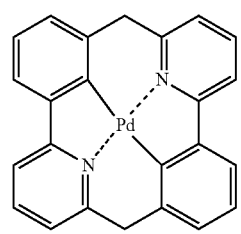
Compound (121)
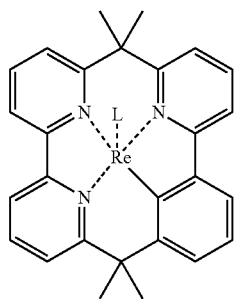
Compound (122)
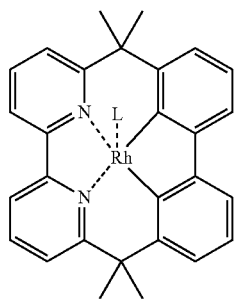
Compound (123)
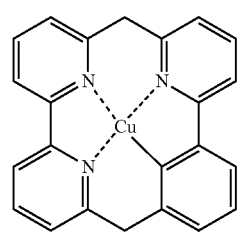
Compound (124)
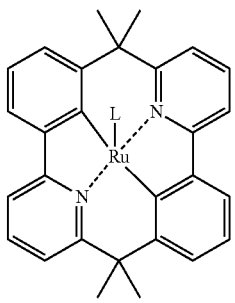
Compound (125)
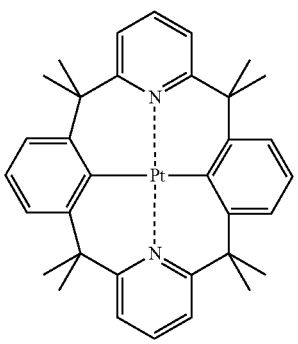
Compound (126)
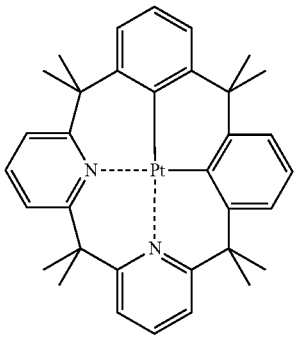
Compound (127)
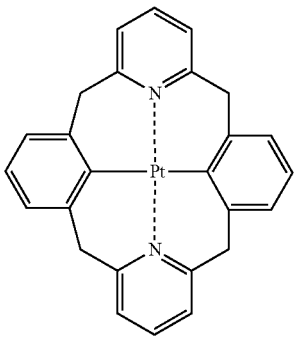

Compound (128)
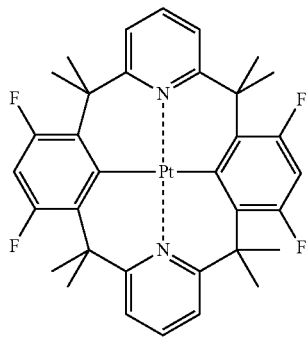
Compound (132)
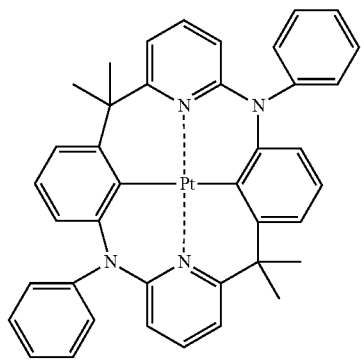
Compound (129)
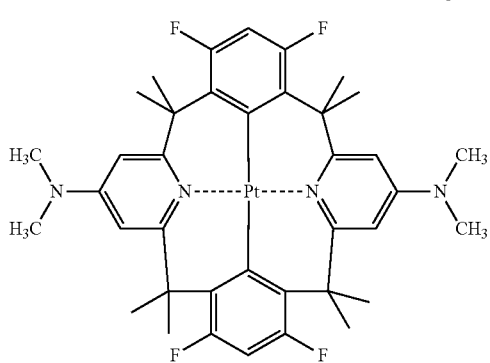
Compound (133)
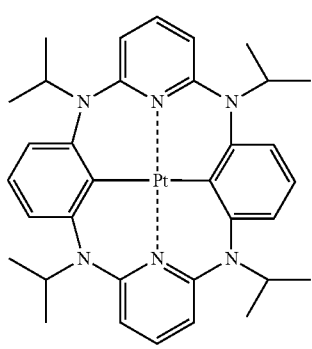
Compound (130)
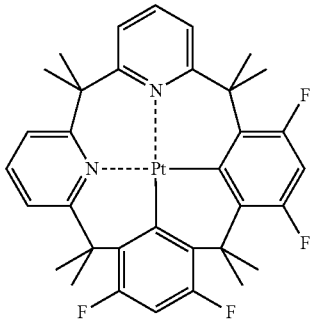
Compound (134)
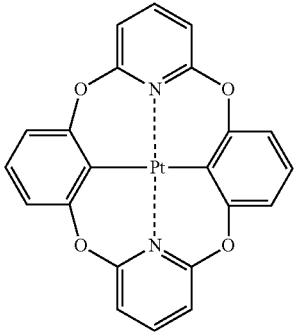
Compound (131)
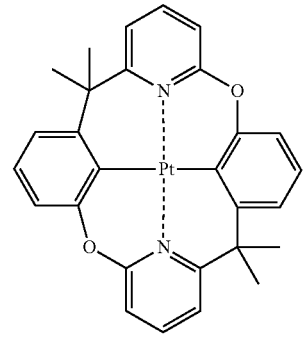
Compound (135)
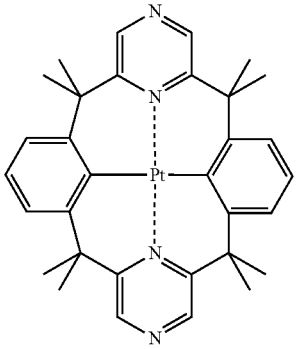

Compound (136)
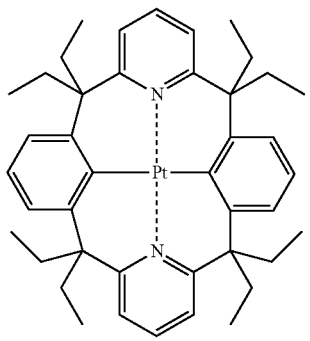
Compound (137)
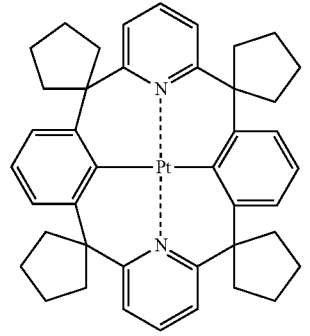
Compound (138)
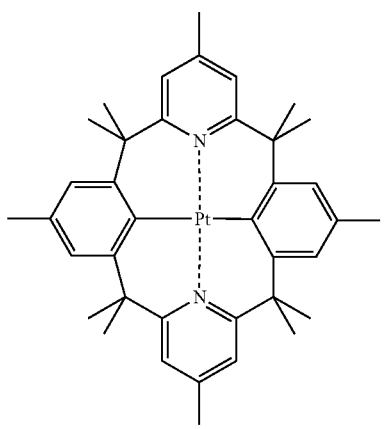
Compound (139)
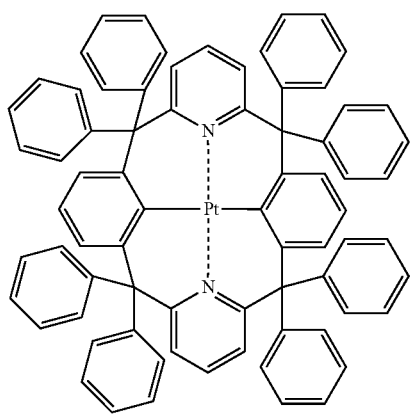
Compound (140)
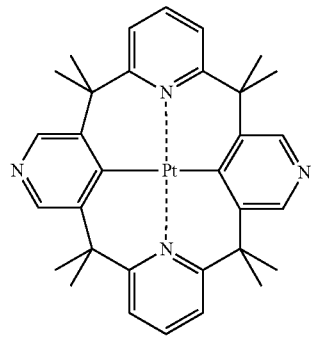
Compound (141)
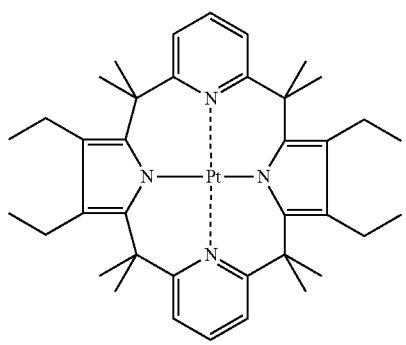
Compound (142)
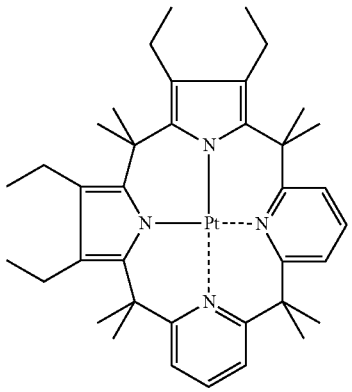
Compound (143)
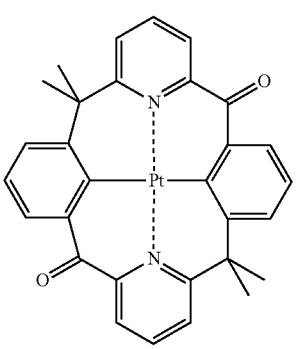

Compound (144)
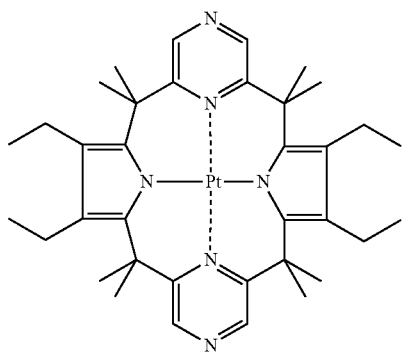
Compound (148)
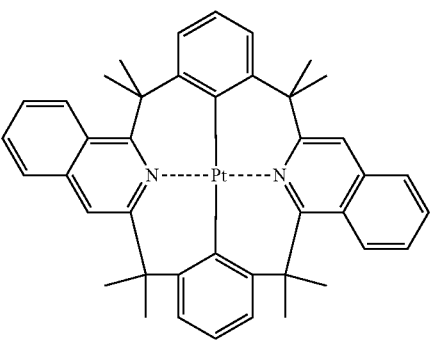
Compound (145)
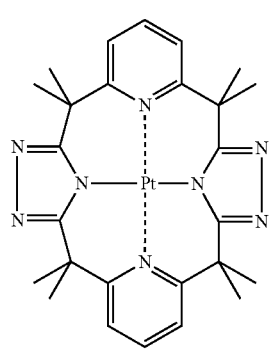
Compound (149)
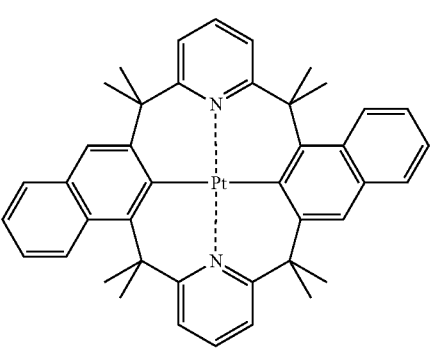
Compound (146)
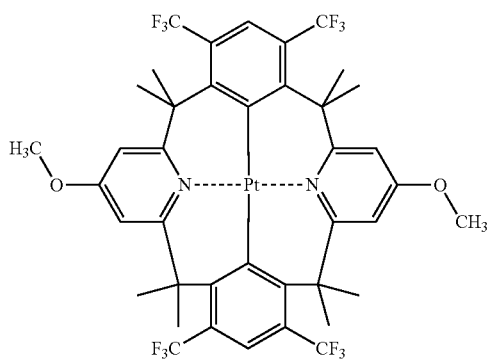
Compound (150)
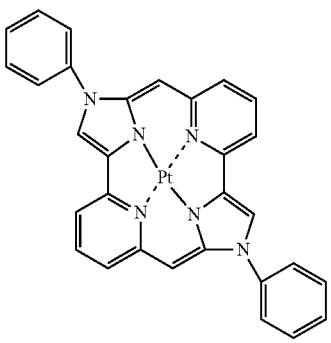
Compound (147)
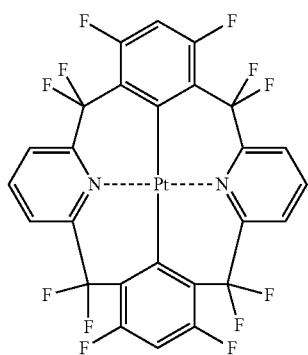
Compound (151)
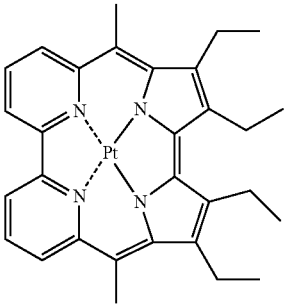

Compound (152)

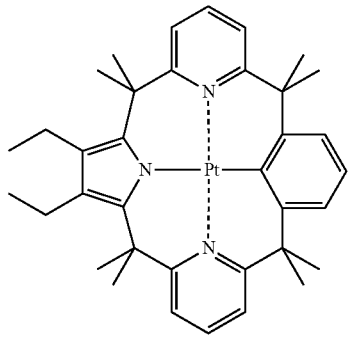

Compound (153)

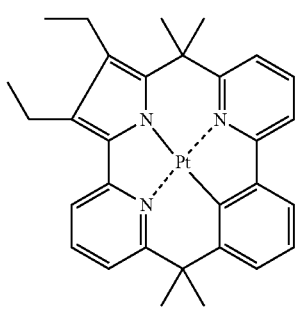

Compound (154)

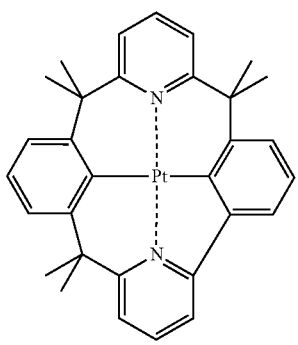

Compound (155)

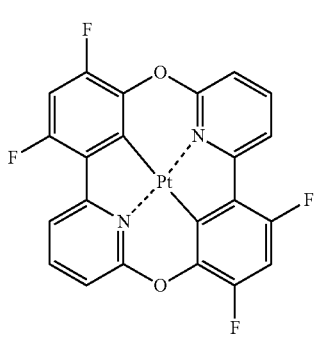

Compound (156)

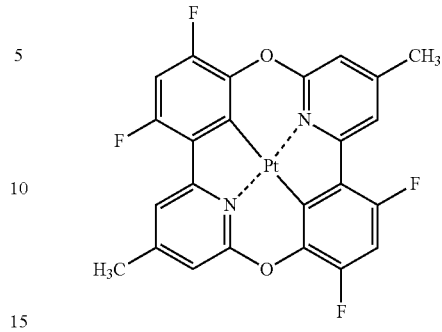

Compound (157)

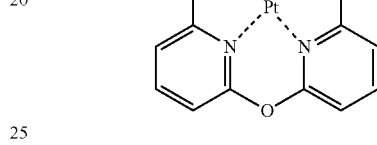

Compound (158)

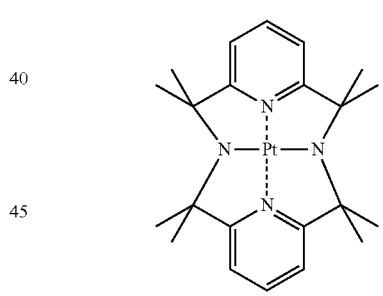

Compound (159)

The compounds of the present invention that are represented by formula (1) can be synthesized according to, for example, the method described in Journal of Chemical Society, 5008 (1952), or synthesis methods described below.

The compounds of the present invention that are represented by formula (1) ($n^{11}=1$) can be synthesized according to various methods. For example, the compounds can be obtained by reacting a ligand or its dissociated product with a compound containing $M^{11}$, in the presence of a solvent (e.g., a halogen-series solvent, an alcohol-series solvent, an ether-series solvent, an ester-series solvent, a ketone-series solvent, a nitrile-series solvent, an amide-series solvent, a sulfone-series solvent, a sulfoxide-series solvent and water), or in the absence of a solvent, in the presence of a base (various inorganic or organic bases, such as sodium methoxide, potassium t-butoxide, triethylamine and potassium carbonate), or in the absence of a base, at room temperature or below, or alternatively by heating (in addition to an ordinary heating, a method of heating by means of microwave is also effective).

A reaction time that is applied in synthesizing the compound of the present invention that is represented by formula (1) ($n^{11}=1$) from a compound containing $M^{11}$ varies depending upon reaction activity, and there is no particular limitation as to the reaction time, but preferably the reaction time is in the range of from 1 minute to 5 days, more preferably in the range of from 5 minutes to 3 days, and furthermore preferably in the range of from 10 minutes to 1 day.

A reaction temperature that is applied in synthesizing the compound of the present invention that is represented by formula (1) ($n^{11}=1$) from a compound containing $M^{11}$ varies depending upon reaction activity, and there is no particular limitation as to the reaction temperature, but the reaction temperature is preferably in the range of from 0° C. to 300° C., more preferably in the range of from 5° C. to 250° C., and furthermore preferably in the range of from 10° C. to 200° C.

The compound of the present invention that is represented by formula (1) ($n^{11}=1$) can be synthesized by adding a ligand that has a partial structure of an objective complex (for example, Compound (I) in synthesis of Compound (8)) preferably in an equivalent amount of from 0.1 to 10, more preferably in an equivalent amount of from 0.3 to 6, furthermore preferably in an equivalent amount of from 0.5 to 4, to a metal compound respectively. As the aforementioned metal compound, there are illustrated a metal halide (e.g., platinum chloride), a metal acetate (e.g., palladium acetate), an acetylacetonato-metal (e.g., acetylacetonatoeuropium), and hydrates of these compounds. The compounds of the present invention that are represented by formula (6) can be obtained by reacting a ligand that has a partial structure of formula (6) (e.g., Compound (1), Compound (9), Compound (14), Compound (21), Compound (24)) with a platinum compound (e.g., $PtCl_2$, $K_2PtCl_4$, $Pt(acac)_2$). The compound represented by formula (1) ($n^{11}=1$) also can be synthesized in the same manner as the compound represented by formula (6). The compounds of the present invention that are represented by formula (6) can be synthesized according to the aforementioned synthesis method of the compound represented by formula (1).

Next, luminescent devices containing a compound of the present invention are explained below.

The luminescent devices of the present invention can employ ordinary luminescent systems, driving methods and using forms, provided that the device uses the compound of the present invention. The compound represented, for example, by formula (1) is preferably used as a luminescent material, or a hole injection material/hole-transporting material. The luminescent material to be used may be ultraviolet emission or infrared emission, or fluorescence emission or phosphorescence emission. As a typical luminescent device, there are organic EL (electroluminescence) devices.

Optical output efficiency of the luminescent device of the present invention can be improved according to various known methods. For example, the optical output efficiency can be improved by processing a surface shape of the substrate (for example, formation of fine uneven pattern), controlling refractive indices among a substrate, an ITO layer and an organic layer(s), or controlling thickness among a substrate, an ITO layer and an organic layer(s). Thereby external quantum efficiency can be improved.

The luminescent device of the present invention may be a so-called top emission system of the device that output light emission from the positive electrode side, as described in, for example, JP-A-2003-208109, JPA-2003-248441, JP-A-2003-257651 and JP-A-2003-282261.

The substrate that can be used in the luminescent device of the present invention is not particularly restricted. Examples of the substrate include inorganic materials, such as zirconia-stabilized yttrium, and glass; polyesters, such as polyethylene terephthalate, polybutylene terephthalate and polyethylene naphthalate; and high molecular weight materials, such as polyethylene, polycarbonate, polyethersulfone, polyarylate, allyldiglycolcarbonate, polyimide, polycycloolefin, norbornene resin, poly(chlorotrifluoroethylene), polytetrafluoroethylene (Teflon (registered trade mark)), and polytetrafluoroethylene/polyethylene copolymers.

The organic electroluminescent device of the present invention may contain a blue-fluorescent compound. Alternatively, a blue luminescent device containing a blue fluorescent compound and the luminescent device of the present invention may be used together, to prepare a multicolor light-emitting device or a full color light-emitting device.

The host material for use in the luminescent device of the present invention may be of one kind, or of two or more kinds. As the host material, are preferable arylamine derivatives (for example, triphenylamine derivatives, benzidine derivatives), aromatic hydrocarbon compounds (for example, triphenylbenzene derivatives, triphenylene derivatives, phenanthrene derivatives, naphthalene derivatives, tetraphenylene derivatives), aromatic nitrogen-containing heterocyclic compounds (for example, pyridine derivatives, pyrazine derivatives, pyrimidine derivatives, triazine derivatives, pyrazole derivatives, imidazole derivatives, oxazole derivatives, pyrrole derivatives), and metal complexes (for example, zinc complexes, aluminum complexes, gallium complexes).

The electroluminescent device of the present invention preferably has, between a negative electrode and a luminescent layer, a layer containing a compound having ionization potential of 5.9 eV or more (more preferably 6.0 eV or more), and more preferably has an electron-transporting layer having ionization potential of 5.9 eV or more.

A method of forming an organic layer of the luminescent device containing the compound of the present invention is not particularly limited. As the method, various methods, such as a resistance heating-utilizing vapor deposition method, an electron-beam method, a sputtering method, a molecular lamination method, a coating method (e.g., a splay coating method, dip coating method, dipping method, roll coating method, gravure coating method, reverse coating method, roll brushing method, air knife coating method, curtain coating method, spin coating method, flow coating method, bar coating method, micro gravure coating method, air doctor coating method, blade coating method, squeeze coating method, transfer roll coating method, kiss coating method, cast coating method, extrusion coating method, wire bar coating method and screen coating method), an inkjet method, a printing method, and a transfer method, can be adopted. From the viewpoints of characteristics and production, a resistance heating-utilized vapor deposition method, a coating method and a transfer method are preferable. A layer of the compound of the present invention may be formed on a substrate, according to any one of the aforementioned forming methods. The layer has no particular limitation as to its thickness, but the layer thickness is preferably 10 nm or more, and more preferably in the range of from 50 nm to 5 μm.

The luminescent device of the present invention is a device having a luminescent layer or at least two thin film layers of organic compounds including a luminescent layer formed between a pair of electrodes, a positive electrode (anode) and a negative electrode (cathode). Examples of the thin layer(s) that the luminescent device may have in addition to the luminescent layer, include a hole injection layer, a hole-transporting layer, an electron injection layer, an electron-transporting layer, a protective layer, and the like. Further, these layers each may have other functions. For forming each layer, various kinds of materials may be used.

The positive electrode is to supply positive holes to a positive hole-injecting layer, a positive hole-transporting layer, a luminescent layer, and the like, and metals, alloys, metal oxides, electrically conductive compounds, or mixtures of these can be used therefor, materials having a work function of 4 eV or more are preferably used. Specific examples of the materials include electrically conductive metal oxides, such as tin oxide, zinc oxide, indium oxide, and indium tin oxide (ITO); metals, such as gold, silver, chromium, and nickel; mixtures or laminations of these metals with electrically conductive metal oxides; inorganic electrically conductive substances, such as copper iodide and copper sulfide; organic electrically conductive substances, such as polyaniline, polythiophene, and polypyrrole; and laminations of these materials with ITO. Electrically conductive metal oxides are preferably used, and ITO is particularly preferably used in view of producibility, high conductivity and transparency. The film thickness of the positive electrode can be selected arbitrarily according to materials to be used, but is generally preferably from 10 nm to 5 nm, more preferably from 50 nm to 1 nm, and still more preferably from 100 nm to 500 nm.

The positive electrode generally comprises a layer(s) formed on a soda-lime glass, non-alkali glass or transparent resin substrate. When a glass substrate is used, non-alkali glass is preferably used for lessening elution of ions from the glass. Further, when soda-lime glass is used, it is preferred to provide a barrier coat such as silica. The thickness of the substrate is not particularly limited so long as it can sufficiently stand mechanical strength. When glass is used, the thickness is generally 0.2 mm or more, preferably 0.7 mm or more.

Various processes are used in the manufacture of the positive electrode according to the materials to be used. In the case of using ITO, for example, a thin layer film(s) is formed by an electron beam process, a sputtering process, a resistance heating vapor deposition process, a chemical reaction process (e.g. a sol-gel process), or the process of coating a dispersion of an indium tin oxide.

It is possible to reduce the driving voltage or increase the luminescent efficacy of the device or element, by the process such as washing of the positive electrode. In the case of using ITO, for example, UV-ozone processing or plasma treatment is effective.

The negative electrode is to supply electrons to an electron-injecting layer, an electron-transporting layer, a luminescent layer, and the like, and the negative electrode is selected taking into consideration the adhesion with the layer adjacent to the negative electrode, such as an electron-injecting layer, electron-transporting layer, or luminescent layer; ionization potential, and stability. As materials of the negative electrode, metals, alloys, metal halides, metal oxides, electrically conductive compounds, or mixtures of these materials can be used. Specific examples include alkali metals (e.g., Li, Na, K) or their fluorides or oxides, alkaline earth metals (e.g., Mg, Ca) or their fluorides or oxides, gold, silver, lead, aluminum, sodium-potassium alloys or mixed metals thereof, lithium-aluminum alloys or mixed metals thereof, magnesium-silver alloys or mixed metals thereof, and rare earth metals, such as indium, ytterbium, and the like; preferably materials having a work function of 4 eV or less, and more preferably aluminum, lithium-aluminum alloys or mixed metals thereof, and magnesium-silver alloys or mixed metals thereof. The negative electrode structure may be not only a single layer of the aforementioned compound or mixture thereof, but also a laminate comprised of the aforementioned compound or mixture thereof. For example, laminate structures of aluminum/ lithium fluoride, or aluminum/lithium oxide are preferable. The film thickness of the negative electrode can be selected arbitrarily according to materials to be used, but is generally preferably from 10 nm to 5 µm, more preferably from 50 nm to 1 µm, and still more preferably from 100 nm to 1 µm.

Processes such as an electron beam process, a sputtering process, a resistance heating vapor deposition process, a coating process, and a transfer method are used in the manufacture of the negative electrode, and a single metal can be vapor-deposited or two or more components can be vapor-deposited at the same time. Further, a plurality of metals can be vapor-deposited at the same time to form an alloy electrode, alternatively a previously prepared alloy can be vapor-deposited.

It is preferred that the sheet resistance of the positive electrode and the negative electrode be low, preferably several hundreds Ω/□ or less.

The material for a luminescent layer may be any of materials capable of forming a layer that can function so as to accept both injection of holes from the positive electrode, the hole injection layer or the hole-transporting layer and injection of electrons from the negative electrode, the electron injection layer or the electron-transporting layer when electric field is applied thereto, or to let the charges injected therein to transfer, or to enable the emission of light by providing a cite for recombining the holes and the electrons. Besides the compound of the present invention, examples of the material include various metal complexes typically exemplified by metal complex or rare earth complex of benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, perylene derivatives, perinone derivatives, oxadiazole derivatives, aldazine derivatives, pyraridine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, aromatic dimethylidyne compounds, and 8-quinolinol derivatives; polymeric compounds, such as polythiophene, polyphenylene, and polyphenylenevinylene; organic silanes; transition metal complexes (e.g., iridium trisphenylpyridine and platinum porphyrin, and derivatives thereof). The film thickness of the luminescent layer is not particularly restricted, but it is generally preferably from 1 nm to 5 mm, more preferably from 5 nm to 1 µm, and still more preferably from 10 nm to 500 nm.

Although there is no particular limitation on methods for forming the luminescent (light emitting) layers, methods such as resistance heating vapor deposition, electron beam processing, sputtering, molecular lamination, coating, inkjet process, printing, LB processing, and transfer process can be used. Preferred are a resistance heating vapor deposition method and a coating method.

The luminescent layer may be formed of a single compound, or two or more kinds of compounds. Further, the luminescent layer may have a single layer structure, or a multiple-layer structure made of at least two layers. Each layer may emit light of a different luminescent color so that the luminescent layer can emit, for example, a white light. A single luminescent layer may emit a white light. When the luminescent layer is a plurality of layers, each layer may be formed of a single material, or at least two compounds or materials.

Materials of the positive hole-injecting layer and the positive hole-transporting layer are sufficient if they have any of the functions of injecting positive holes from the positive electrode, transporting positive holes, and blocking the electrons injected from the negative electrode. Specific examples of the materials include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne-series compounds, porphyrin-series compounds, polysilane-series compounds, poly(N-vinylcarbazole) derivatives, aniline-series copolymers, electrically conductive high molecular weight oligomers, such as thiophene oligomers and polythiophene; organic silane compounds, carbon film, and the compounds of the present invention. The film thickness of the hole-injection layer is not particularly limited, and in general, it is preferably from 1 nm to 5 μm, more preferably from 1 nm to 100 nm, and further preferably from 1 nm to 10 nm. The film thickness of the hole-transporting layer is not particularly limited, and in general, it is preferably from 1 nm to 5 μm, more preferably from 5 nm to 1 μm, and further preferably from 10 nm to 500 nm. The hole-injecting layer or hole-transporting layer may have a single layer structure of one kind or two or more kinds of the above materials, or alternatively, a multilayer structure comprising plural layers having the same composition or different compositions.

Examples of a method of forming the hole-injecting layer and the hole-transporting layer include a vacuum deposition method, an LB method, the process of dissolving or dispersing the above-described hole-injecting/transporting material in a solvent and coating; an ink jet method, a printing method, and a transfer method. In the case of a coating process, a positive hole-injecting/transporting material can be dissolved or dispersed with a resin component. Examples of such resin components include polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin, silicone resin, and the like.

Materials of the electron-injecting layer and the electron-transporting layer are sufficient if they have any of the functions of injecting electrons from the negative electrode, transporting electrons, and blocking (as a barrier off) the positive holes injected from the positive electrode. Specific examples of the materials include triazole derivatives, oxazole derivatives, oxadiazole derivatives, imidazole derivatives, fluorenone derivatives, anthraquinodimethane derivatives, anthrone derivatives, diphenylquinone derivatives, thiopyrandioxide derivatives, carbodiimide derivatives, fluorenylidenemethane derivatives, distyrylpyrazine derivatives, tetracarboxylic acid anhydrides of aromatic rings such as naphthalene and perylene, phthalocyanine derivatives, various metal complexes represented by metal complexes of 8-quinolinol derivatives, metallophthalocyanines and metal complexes having benzoxazole or benzothiazole ligands, organosilane compounds. The film thickness of the electron-injecting layer and the electron-transporting layer is not particularly restricted, but it is generally preferably from 1 nm to 5 μm, more preferably from 5 nm to 1 μm, and still more preferably from 10 nm to 500 nm. The electron-injecting layer and the electron-transporting layer may be single layer structure comprising one or two or more of the above materials, or may be multilayer structure comprising a plurality of layers of the same composition or different compositions.

Examples of a method of forming the electron injecting layer and the electron transporting layer include a vacuum deposition method, an LB method, the process of dissolving or dispersing the above-described electron-injecting/transporting material in a solvent and coating; an ink jet method, a printing method, and a transfer method. In the case of a coating process, an electron injecting/transporting material can be dissolved or dispersed with a resin component. As the resin components, for example, those exemplified in the positive hole-injecting and transporting layers can be applied.

Materials of the protective layer are sufficient if they have the function of preventing substances which accelerate deterioration of the device or element, such as water or oxygen, from entering the device or element. Specific examples of the materials include metals such as In, Sn, Pb, Au, Cu, Ag, Al, Ti and Ni; metal oxides such as MgO, SiO, $SiO_2$, $Al_2O_3$, GeO, NiO, CaO, BaO, $Fe_2O_3$, $Y_2O_3$ and $TiO_2$; metal fluorides such as $MgF_2$, LiF, $AlF_3$ and $CaF_2$; metal nitrides such as $SiN_x$ and $SiO_xN_y$; polyethylene, polypropylene, polymethyl methacrylate, polyimide, polyurea, polytetrafluoroethylene, polychlorotrifluoroethylene, polydichlorodifluoroethylene, copolymers of chlorotrifluoroethylene and dichlorodifluoroethylene, copolymers prepared by copolymerizing a monomer mixture of tetrafluoroethylene and at least one comonomer, fluorine-containing copolymers having cyclic structures on the main chain, water-absorbing substances having a water absorption rate of at least 1%, and moisture-proof substances having a water absorption rate of at most 0.1%.

The forming process of the protective layer is also not particularly restricted, and, for example, a vacuum deposition process, a sputtering process, a reactive sputtering process, an MBE (molecular beam epitaxy) process, a cluster ion beam process, an ion-plating process, a plasma polymerization process (a high frequency exciting ion-plating process), a plasma CVD process, a laser CVD process, a heat CVD process, a gas source CVD process, a coating process, a printing process, and a transfer process can be applied.

The luminescent device of the present invention is excellent in luminescent properties and long in life. Further, the novel platinum compound of the present invention is preferable, for example, for producing the luminescent device.

EXAMPLES

The present invention will be explained in more detail with reference to the examples below, but the embodiments for carrying out the present invention should not be construed to be limited to these.

Synthesis of Compound (1)

Compound (1) was synthesized, according to the method described in Journal of Chemical Society, 5008 (1952). That is, 40 ml of n-butanol was added to 6 g of 1,3-diiminoindoline and 4.6 g of 2,6-diaminopyridine, followed by heating under reflux for 9 hours. After cooling to room temperature, the reaction mixture was filtered. The precipitate was washed with 40 ml of n-butanol and dispersed in 50 ml of nitrobenzene. After the dispersion was heated under reflux, recrystallization was conducted by cooling, to yield 7 g of Compound (I).

With respect to the thus-obtained compound, a peak of m/z=440 was detected in DP-EI-MS measurement.

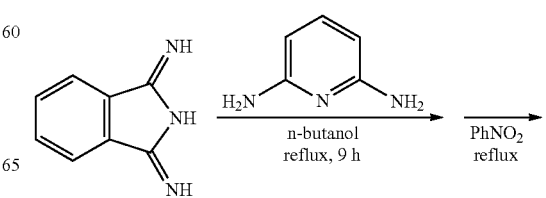

-continued

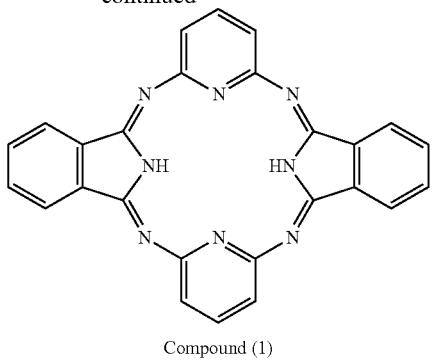

Compound (1)

Synthesis of Compound (8)

To 0.1 g of Compound (I) and 0.21 g of $PtCl_2$, 10 ml of benzonitrile was added, followed by stirring, at an inner temperature of 160° C. under a nitrogen atmosphere, for 4 hours. After cooling to room temperature, the reaction mixture was filtered. The precipitate was washed with 20 ml of benzonitrile and 30 ml of methanol, to yield 0.05 g of Compound (8).

With respect to the thus-obtained compound, a peak of m/z=633 was detected in DP-EI-MS measurement.

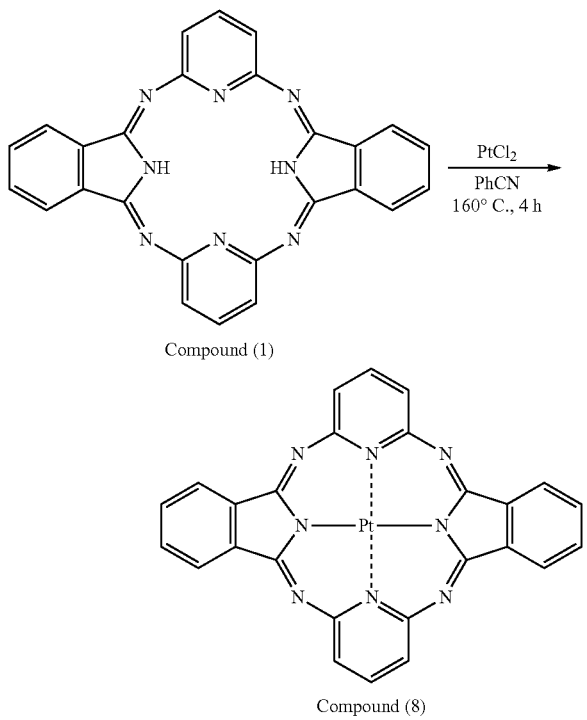

Comparative Example 1

A cleaned ITO substrate was placed in a vapor deposition apparatus, and on the substrate, CuPc (copper phthalocyanine) was vapor-deposited, to form a film of 10 nm thickness, and then α-NPD (4,4'-bis-[N-(1-naphthyl)-N-phenylamino]biphenyl) was vapor-deposited, to form a film of 40 nm thickness, and then $Alq_3$ (tris(8-hydroxyquinolinato)aluminum complex) was vapor-deposited, to form a film of 60 nm thickness, in this order. Then, a patterned mask (for adjusting each emission area to 4 mm×5 mm) was set on the above-obtained organic thin layers, and further thereon, in the vacuum deposition apparatus, lithium fluoride was vapor-deposited, to form a film of 3 nm thickness, followed by vapor-deposition of a 400 nm-thick Al film. The thus-produced EL device was subjected to luminescence by applying, thereto, a DC constant voltage, by means of a source measure unit, Model 2400 (trade name), made by Toyo Technica Co., Ltd., and the luminance shown by the EL device was measured using a luminometer DM-8 (trade name), made by Topcon Co. As a result of the measurement, the light emission given by the EL device was found to be a green luminescence of 200 $cd/m^2$ with quantum efficiency of 1.1%. After the EL device was subjected to luminescence of 100 $cd/m^2$ for 10 hours, dark spots were observed with the naked eye.

Example 1

A cleaned ITO substrate was placed in a vapor deposition apparatus, and on the substrate, Compound (8) of the present invention was vapor-deposited, to form a film of 5 nm thickness, and then α-NPD (4,4'-bis-[N-(1-naphthyl)-N-phenylamino]biphenyl) was vapor-deposited, to form a film of 60 nm thickness, and then $Alq_3$ (tris(8-hydroxyquinolinato)aluminum complex) was vapor-deposited, to form a film of 40 nm thickness, in this order. Then, a patterned mask (for adjusting each emission area to 4 mm×5 mm) was set on the above-obtained organic thin layers, and further thereon, in the vacuum deposition apparatus, lithium fluoride was vapor-deposited, to form a film of 3 nm thickness, followed by vapor-deposition of a 400 nm-thick Al film. The thus-produced EL device was subjected to luminescence by applying, thereto, a DC constant voltage, by means of a source measure unit, Model 2400, made by Toyo Technica Co., Ltd., and the luminance shown by the EL device was measured using a luminometer BM-8, made by Topcon Co. As a result of the measurement, it was found that the EL device gave a green luminescence of 200 $cd/m^2$ with quantum efficiency of 1.4%. After the EL device was subjected to luminescence of 100 $cd/m^2$ for 10 hours, no dark spots were observed with the naked eye.

Similarly, by employing other compounds of the present invention, luminescent devices giving high luminous efficiency and long life can also be produced. In addition, the compounds of the present invention enable to emit a blue to green phosphorescence, and therefore blue to green luminescent devices containing the compound of the present invention can be prepared.

INDUSTRIAL APPLICABILITY

The luminescent device of the present invention is able to give high luminous efficiency. The luminescent device of the present invention can be preferably used in such fields as display devices, displays, backlights, electrophotography, illuminating light sources, recording light sources, exposing light sources, reading light sources, signs, signboards, interiors, and optical communications. Further, the compounds of the present invention can be utilized for the electroluminescent devices, as well as medical usage, brightening agents, photographic materials, UV absorbing materials, laser dyes, recording media materials, inkjet pigments, color filter dyes, color conversion filters, and the like.

Having described our invention as related to the present embodiments, it is our intention that the invention not be limited by any of the details of the description, unless otherwise specified, but rather be construed broadly within its spirit and scope as set out in the accompanying claims.

The invention claimed is:

1. An organic electroluminescent device, comprising a pair of electrodes, and at least one organic layer including a luminescent layer between the electrodes, wherein said organic layer comprises at least one compound represented by formula (16) or a tautomer thereof:

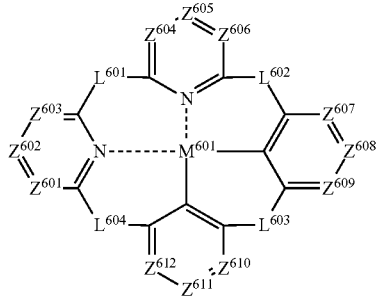

Formula (16)

wherein, in formula (16), $Z^{601}$, $Z^{602}$, $Z^{603}$, $Z^{604}$, $Z^{605}$, $Z^{606}$, $Z^{607}$, $Z^{608}$, $Z^{609}$, $Z^{610}$, $Z^{611}$, and $Z^{612}$ each independently represents CR, CH, or N, wherein R represents a substituent; $L^{601}$, $L^{602}$, $L^{603}$ and, $L^{604}$ each represent a single bond or a linking group; and $M^{601}$ represents a metal ion that may further have at least one ligand.

2. An organic electroluminescent device, comprising a pair of electrodes, and at least one organic layer including a luminescent layer between the electrodes, wherein said organic layer comprises at least one compound represented by formula (17) or a tautomer thereof:

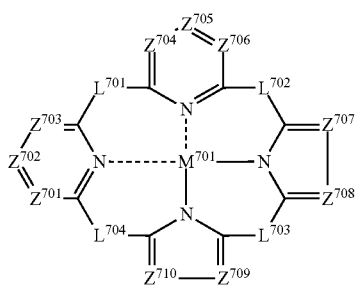

Formula 17 wherein, in formula (17), $Z^{701}$, $Z^{702}$, $Z^{703}$, $Z^{704}$, $Z^{705}$, $Z^{706}$, $Z^{707}$, $Z^{708}$, $Z^{709}$, and $Z^{710}$ each independently represents CR, CH, or N, wherein R represents a substituent; $L^{701}$, $L^{702}$, $L^{703}$ and $L^{704}$ each represent a single bond or a linking group; and $M^{701}$ represents a metal ion that may further have at least one ligand.

3. An organic electroluminescent device, comprising a pair of electrodes, and at least one organic layer including a luminescent layer between the electrodes, wherein said organic layer comprises at least one compound represented by formula (18) or a tautomer thereof:

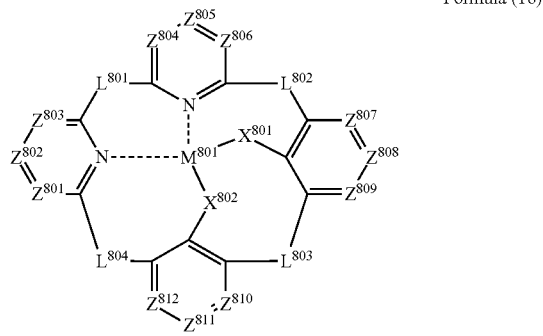

Formula (18)

wherein, in formula (18), $Z^{801}$, $Z^{802}$, $Z^{803}$, $Z^{804}$, $Z^{805}$, $Z^{806}$, $Z^{807}$, $Z^{808}$, $Z^{809}$, $Z^{810}$, $Z^{811}$, and $Z^{812}$ each independently represents CR, CH, or N, wherein R represents a substituent; $L^{801}$, $L^{802}$, $L^{803}$ and $L^{804}$ each represent a single bond or a linking group; $M^{801}$ represents a metal ion that may further have at least on ligand; and $X^{801}$ and $X^{802}$ each represent an oxygen atom, a substituted or unsubstituted nitrogen atom, or a sulfur atom.

\* \* \* \* \*